United States Patent
Old et al.

(10) Patent No.: US 7,803,797 B2
(45) Date of Patent: Sep. 28, 2010

(54) SUBSTITUTED ARYLCYCLOPENTENES AS THERAPEUTIC AGENTS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/427,803

(22) Filed: Apr. 22, 2009

(65) Prior Publication Data

US 2009/0270385 A1     Oct. 29, 2009

Related U.S. Application Data

(60) Provisional application No. 61/047,609, filed on Apr. 24, 2008.

(51) Int. Cl.
| | |
|---|---|
| A61K 31/381 | (2006.01) |
| A61K 31/5377 | (2006.01) |
| A61K 31/341 | (2006.01) |
| A61K 31/426 | (2006.01) |
| A61K 31/421 | (2006.01) |
| C07D 277/34 | (2006.01) |
| C07D 277/24 | (2006.01) |
| C07D 263/32 | (2006.01) |
| C07D 413/12 | (2006.01) |
| C07D 333/16 | (2006.01) |
| C07D 307/38 | (2006.01) |

(52) U.S. Cl. .......... 514/231.5; 514/235.5; 514/438; 514/461; 548/182; 548/204; 548/236; 544/111; 544/145; 544/147; 549/71; 549/499

(58) Field of Classification Search .......... 514/231.5, 514/235.5, 438, 461; 548/182, 204, 236; 549/71, 499; 544/111, 145, 147
See application file for complete search history.

(56) References Cited

U.S. PATENT DOCUMENTS

| | | | |
|---|---|---|---|
| 5,462,968 A | 10/1995 | Woodward | |
| 5,476,872 A | 12/1995 | Garst | |
| 5,698,598 A | 12/1997 | Woodward | |
| 6,090,847 A | 7/2000 | Woodward | |
| 6,437,146 B1 | 8/2002 | Hattori | |
| 6,710,072 B2 | 3/2004 | Burk | |
| 7,091,231 B2 | 8/2006 | Donde | |
| 7,507,817 B2 * | 3/2009 | Old et al. ............ | 544/106 |
| 2002/0094981 A1 | 7/2002 | Ponticello | |
| 2007/0254920 A1 | 11/2007 | DeLong | |
| 2009/0270386 A1 * | 10/2009 | Old et al. ............ | 514/231.5 |

FOREIGN PATENT DOCUMENTS

| | | |
|---|---|---|
| BE | 900959 | 5/1985 |
| WO | WO 2006/083841 | 8/2006 |
| WO | WO 2007/149829 | 12/2007 |
| WO | WO 2008/041054 | 4/2008 |
| WO | WO 2008/064039 | 5/2008 |

OTHER PUBLICATIONS

U.S. Appl. No. 12/523,409, filed Jul. 2009, Old et al.*
Anderson, KE; et al.: Oxadiazoles as Bioisosteric Transformations of Carboxylic Functionalities. II. Eur. J. Med. Chem. 1996, 31, 417-425.
Carey, Francis A.: Organic Chemistry, New York: McGraw-Hill Book Company 1987, p. 63.
Drysdale et al. Rationally Designed "Dipeptoid" Analogues of CCK. Acid Mimics of the Potent and Selective Non-Peptide CCK-B Receptor Antagonist CI-988. J. Med. Chem. 1992, 35, 2573-2581.
Han, Wei; et al.: Investigation of Glycine α-ketoamide HCV NS3 Protease Inhibitors: Effect of Carboxylic Acid Isosteres. Biorganic & Medicinal Chemistry Letters 15 (2005) 3487-3490.
Kohara, Yasuhisa; et al.: Synthesis and Angiotensin II Receptor Antagonist Activities of Benzimidazole Derivatives Bearing Acidic Heterocycles as Novel Tetrazole Bioisosteres. J. Med. Chem. 1996, 39, 5228-5235.
Orlek, Barry; et al.: Comparison of Azabicyclic Esters and Oxadiazoles as Ligands for the Muscarinic Receptor. J. Med. Chem. 1991, 34, 2726-2735.
Silverman, Richard B., The Organic Chemistry of Drug Design and Drug Action, 2nd Edition, Amsterdam: Elsevier Academic Press, 2004, p. 29.
U.S. Appl. No. 60/757,696, filed Jan. 10, 2006, Old.
U.S. Appl. No. 60/805,285, filed Jun. 20, 2006, Old.
U.S. Appl. No. 60/886,018, filed Jan. 22, 2007, Old.

* cited by examiner

*Primary Examiner*—Kamal A Saeed
*Assistant Examiner*—Michael Barker
(74) *Attorney, Agent, or Firm*—Kevin J. Forrestal; John E. Wurst; Doina G. Ene

(57) ABSTRACT

Compounds comprising

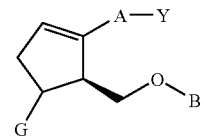

or a pharmaceutically acceptable salt or a prodrug thereof, are disclosed, wherein G, B, Y, and A are as described.

Methods, compositions, and medicaments related thereto are also disclosed.

11 Claims, No Drawings

SUBSTITUTED ARYLCYCLOPENTENES AS THERAPEUTIC AGENTS

RELATED APPLICATION

This application claims the benefit of U.S. Provisional Application Ser. No. 61/047,609, filed Apr. 24, 2008, the disclosure of which is hereby incorporated in its entirety herein by reference

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

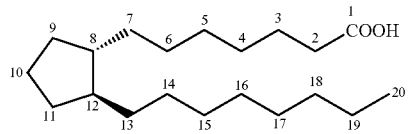

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

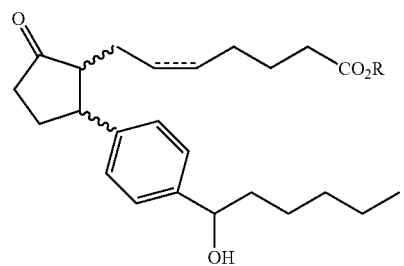

Other $EP_2$ selective agonists are disclosed in U.S. patent application Ser. No. 11/009,298, filed Dec. 10, 2004 (now U.S. Pat. No. 7,091,231 issued Aug. 15, 2006). Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, baldness, the stimulation of hair growth, and the stimulation of the conversion of vellus hair to terminal hair. The compounds themselves are disclosed below.

Disclosed herein is a compound of the formula

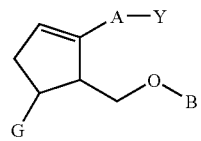

or a pharmaceutically acceptable salt or a prodrug thereof;

Y is

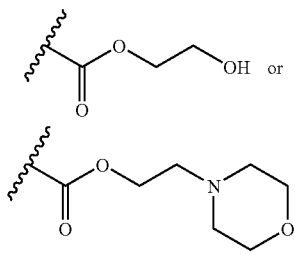

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

G is H or OH; and

B is aryl or heteroaryl.

These compounds are useful for treating glaucoma or ocular hypertension.

The definitions, explanations, and examples provided in this document shall be used to determine the meaning of a particular term or expression where there is any ambiguity arising from any disclosure incorporated by reference herein.

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or C≡C—.

Thus, while not intending to be limiting, A may be —$(CH_2)_6$—, cis —$CH_2CH$=$CH$—$(CH_2)_3$—, or —$CH_2C$≡$C$—$(CH_2)_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

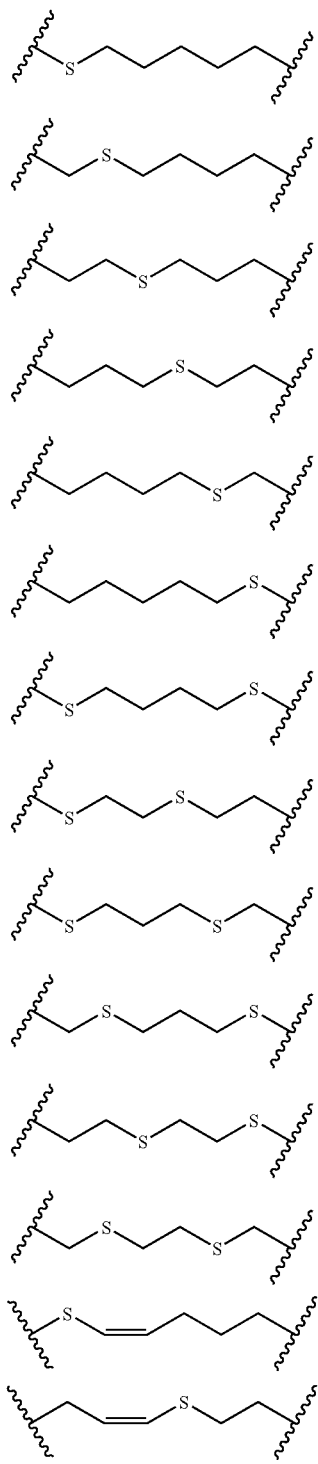

-continued

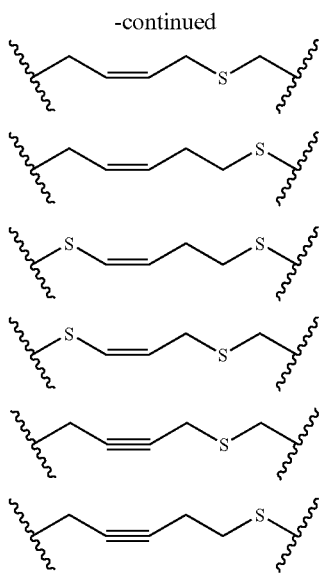

Alternatively, while not intending to limit the scope of the invention in any way, A may be a moiety where O replaces one or two carbon atoms such as one of the following or the like.

-continued

Alternatively, while not intending to limit the scope of the invention in any way, A may have an O replacing one carbon atom and an S replacing another carbon atom, such as one of the following or the like.

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH=CH— or —C≡C—. In other words, while not intending to limit the scope of the invention in any way, In one embodiment A comprises:
1) a) 1, 2, 3, or 4 CH$_2$ moieties, or
   b) 0, 1 or 2 CH$_2$ moieties and —CH=CH— or —C≡C—; and
2) Ar;

e.g. —CH$_2$—Ar—, —(CH$_2$)$_2$—Ar—, —CH═CH—Ar—, —C≡C—Ar—, —CH$_2$—Ar—CH$_2$—, —CH$_2$Ar—(CH$_2$)$_2$—, —CH$_2$Ar—CH═CH—, —CH$_2$Ar—C≡C—, —(CH$_2$)$_2$—Ar—(CH$_2$)$_2$—, and the like;

In another embodiment A comprises:
1) a) O; and 0, 1, 2, or 3 CH$_2$ moieties; or
   b) O; and 0 or 1 CH$_2$ moieties and —CH═CH— or —C≡C—; and
2) Ar;

e.g., —O—Ar—, Ar—CH$_2$—O—, —O—Ar—(CH$_2$)$_2$—, —OAr—CH═CH—, —O—Ar—C≡C—, —O—CH$_2$—Ar—, —O—CH$_2$—Ar—(CH$_2$)$_2$, —O—CH$_2$Ar—CH═CH—, —O—CH$_2$Ar—C≡C—, and the like; or In another embodiment A comprises:
1) a) S; and 0, 1, 2, or 3 CH$_2$ moieties; or
   b) S; and 0 or 1CH$_2$ moieties and —CH═CH— or —C≡C—; and
2) Ar;

e.g., —S—Ar—, Ar—CH$_2$—S—, —S—Ar—(CH$_2$)$_2$—, —SAr—CH═CH—, —S—Ar—C≡C—, —S—CH$_2$—Ar—, —S—CH$_2$—Ar—(CH$_2$)$_2$, —S—CH$_2$Ar—CH═CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$ may be replaced by —CH═CH— or —C≡C—.

In another embodiment, the sum of m and o is 3 wherein one CH$_2$ may be replaced with S or O and 1 —CH$_2$—CH$_2$ may be replaced by —CH═CH— or —C≡C—.

In another embodiment, the sum of m and o is 2 wherein one CH$_2$ may be replaced with S or O or 1 —CH$_2$—CH$_2$ may be replaced by —CH═CH— or —C≡C—.

In another embodiment, the sum of m and o is 4 wherein one CH$_2$ may be replaced with S or O and 1 —CH$_2$—CH$_2$ may be replaced by —CH═CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2$$^-$K$^+$ salt. Any cation of the salt is not counted in the "4 or less heavy atoms." Thus, the substituent may be hydrocarbyl, i.e. a moiety consisting of only carbon and hydrogen, including linear, branched or cyclic hydrocarbyl, and combinations thereof; having up to 4 carbon atoms, including alkyl up to C$_4$, alkenyl, alkynyl, and the like;

hydrocarbyloxy, i.e. —O-hydrocarbyl, up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

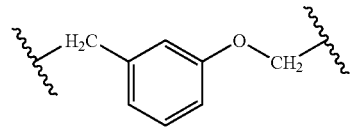

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

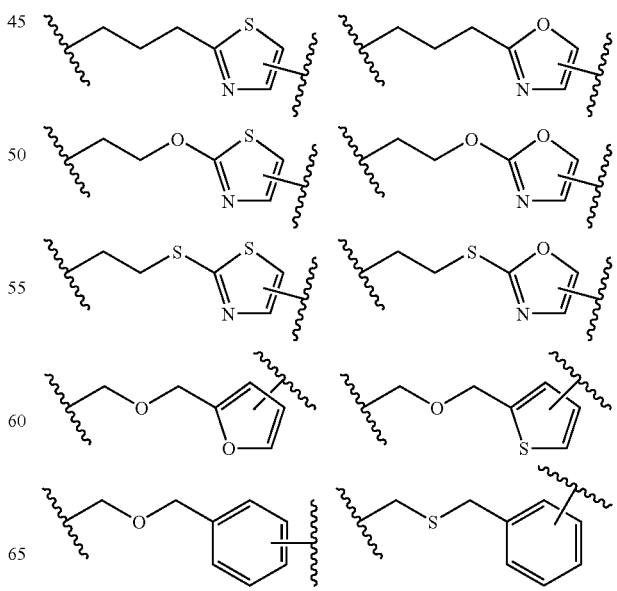

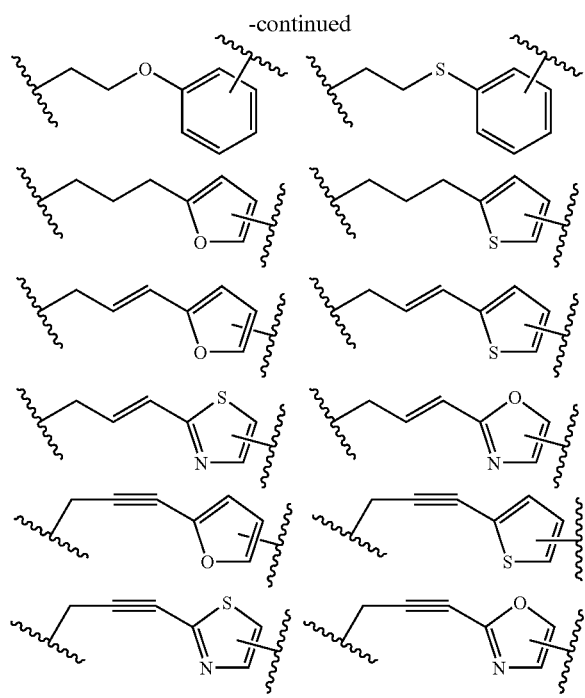

In another embodiment A is —CH₂OCH₂Ar.
In another embodiment A is —CH₂SCH₂Ar.
In another embodiment A is —(CH₂)₃Ar.
In another embodiment A is —CH₂O(CH₂)₄.
In another embodiment A is —CH₂S(CH₂)₄.
In another embodiment A is —(CH₂)₆—.
In another embodiment A is cis —CH₂CH=CH—(CH₂)₃—.
In another embodiment A is —CH₂C≡C—(CH₂)₃—.
In another embodiment A is —S(CH₂)₃S(CH₂)₂—.
In another embodiment A is —(CH₂)₄OCH₂—.
In another embodiment A is cis —CH₂CH=CH—CH₂OCH₂—.
In another embodiment A is —CH₂CH≡CH—CH₂OCH₂—.
In another embodiment A is —(CH₂)₂S(CH₂)₃—.
In another embodiment A is —CH₂-Ph-OCH₂—, wherein Ph is interphenylene.
In another embodiment A is —CH₂-mPh-OCH₂—, wherein mPh is m-interphenylene.
In another embodiment A is —CH₂—O—(CH2)₄—.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

In other embodiments, A is selected from the group:

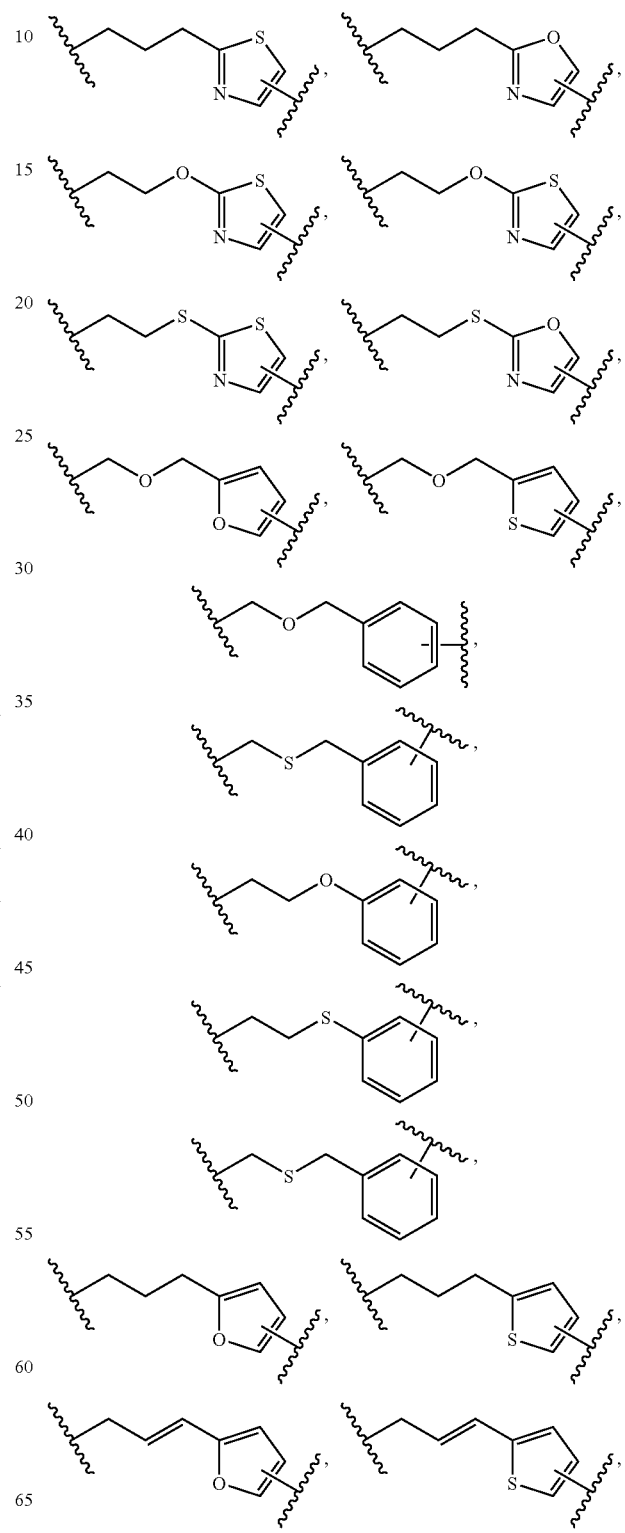

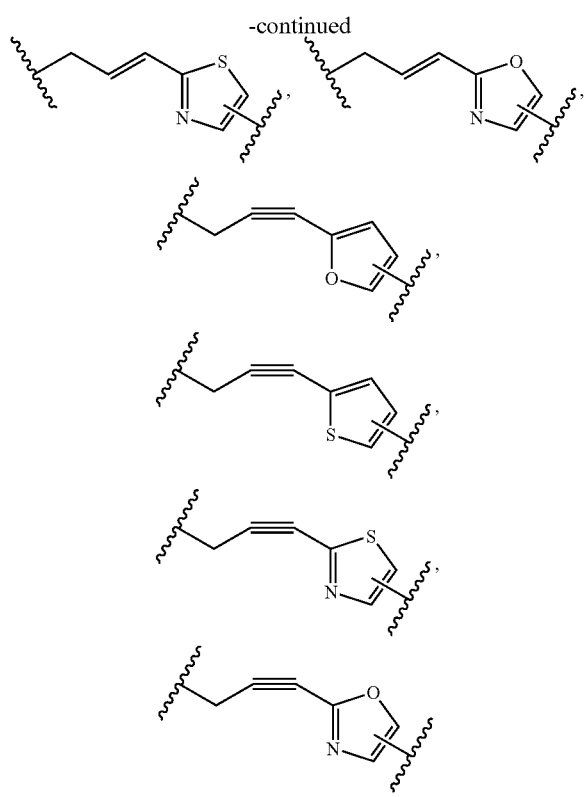

G is H or OH. Thus, compounds according to one of the following structures are possible.

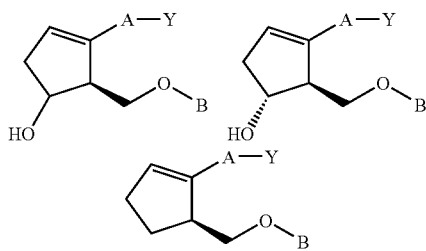

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl should be stable and may have up to 20 non-hydrogen atoms each and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. In addition to the atoms listed above, a substituent may also have a metal cation or other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the 20 non-hydrogen atoms. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH, including hydroxyalkyl, such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_3$OH), NHCH$_3$, and the like;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting—B herein, where—is a bond, the bond is a direct bond to an aromatic ring.

Hydrocarbyl is a moiety consisting of carbon and hydrogen, including, but not limited to:

1. alkyl, which is hydrocarbyl containing no double or triple carbon-carbon bonds; alkyl includes, but is not limited to:
   linear alkyl, cyclic alkyl, branched alkyl, and combinations thereof;
   $C_{1-3}$ alkyl, which refers to alkyl having 1, 2, or 3 carbon atoms, including, but no limited to, methyl, ethyl, isopropyl, cyclopropyl, n-propyl, and the like;
   $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
   combinations of these terms are possible, and their meanings should be obvious to those of ordinary skill in the art; for example $C_{1-6}$ linear alkyl would refer to $C_{1-6}$ alkyl which is also linear;
2. alkenyl, which is hydrocarbyl containing one or more carbon-carbon double bonds; alkenyl includes, but is not limited to:
   linear alkenyl, cyclic alkenyl, branched alkenyl, and combinations thereof;
   alkenyl having 1, 2, 3, or more carbon-carbon double bonds;

3. alkynyl, which is hydrocarbyl containing one or more carbon-carbon triple bonds; akynyl includes, but is not limited to:
   linear alkynyl, cyclic alkynyl, branched alkynyl, and combinations thereof;
   alkynyl having 1, 2, 3, or more carbon-carbon double bonds;
4. aryl, provided that it contains no heteroatoms either in a ring or as a substituent; and
5. combinations of any of the above;

$C_{1-6}$ hydroxylalkyl is hydroxyalkyl having 1, 2, 3, 4, 5, or 6 carbon atoms.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, and 0, 1, 2 or 3 oxygen atoms.

In another embodiment, B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

In another embodiment, B has 1, 2, 3, or 4 halogen substituents.

In another embodiment, B has 1, 2, 3, or 4 chloro substituents.

In another embodiment, B has 1 chloro substituent.

In another embodiment, B has 2 chloro substituents.

In another embodiment, B has 1, 2, 3, or 4 trifluoromethyl substituents.

In another embodiment, B has 1, 2, or 3 trifluoromethyl substituents.

In another embodiment, B has 1 trifluoromethyl substituent.

In another embodiment, B has 2 trifluoromethyl substituents.

In another embodiment, B has a hydroxyl substituent.

Examples of useful moieties for B are depicted below. Each is individually contemplated as an embodiment.

| Structure: | 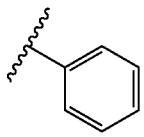 | 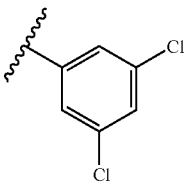 | 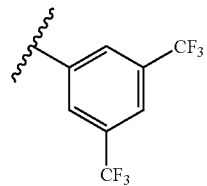 |
|---|---|---|---|
| Name: | unsubstituted phenyl | 3,5-dichlorophenyl | 3,5-di(trifluoromethyl)phenyl |

| Structure: | 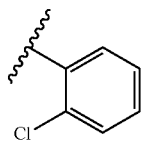 | 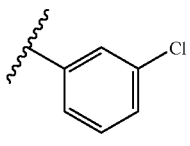 | 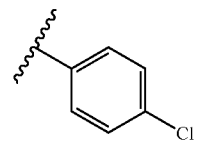 |
|---|---|---|---|
| Name: | 2-chlorophenyl | 3-chlorophenyl | 4-chlorophenyl |

| Structure: | 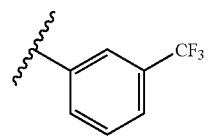 | 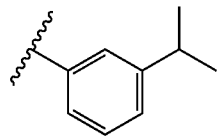 | 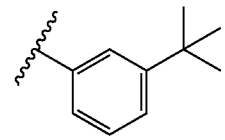 |
|---|---|---|---|
| Name: | 3-(trifluoromethyl)phenyl | 3-isopropylphenyl | 3-tert-butylphenyl |

-continued
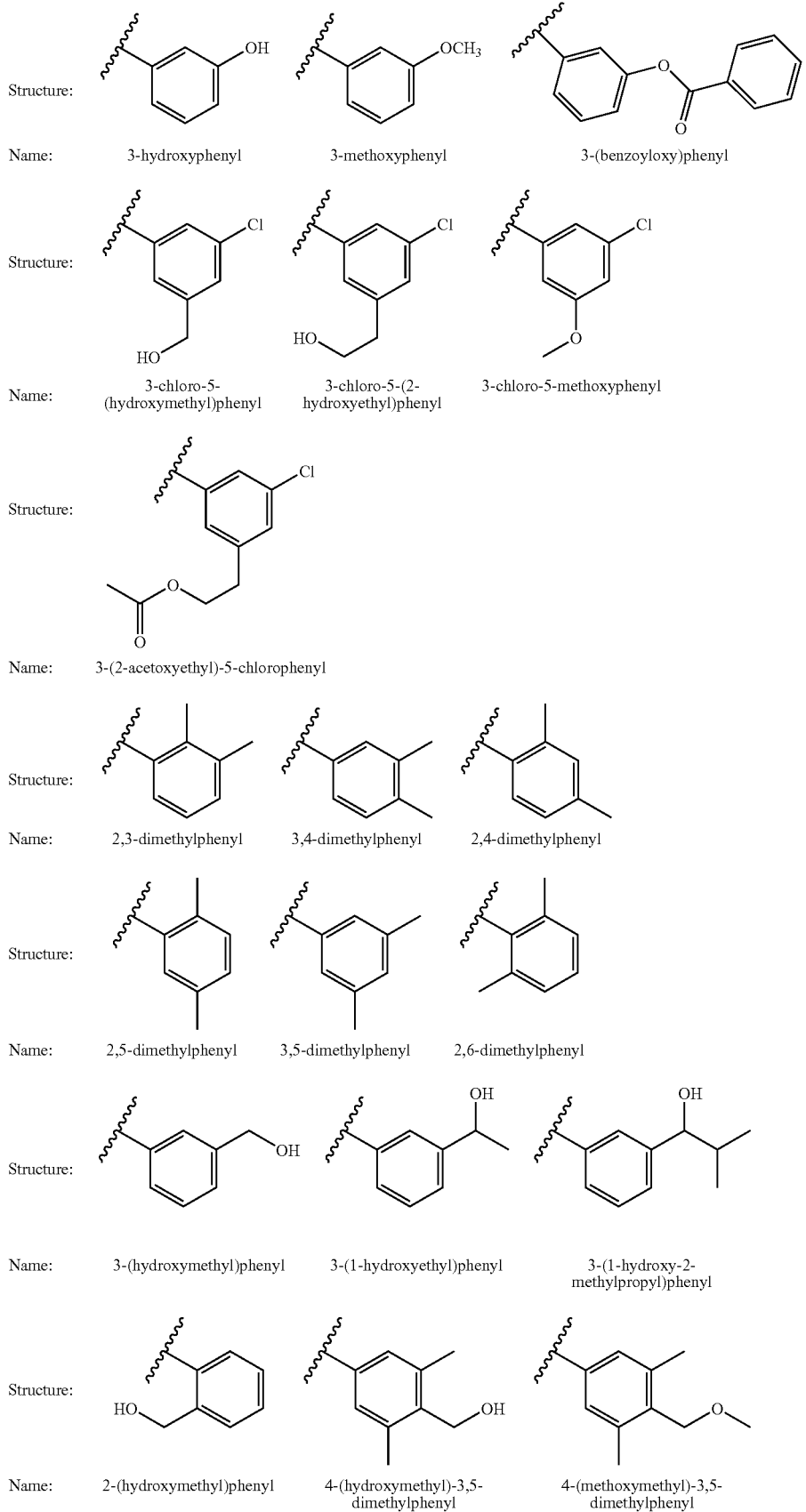

-continued
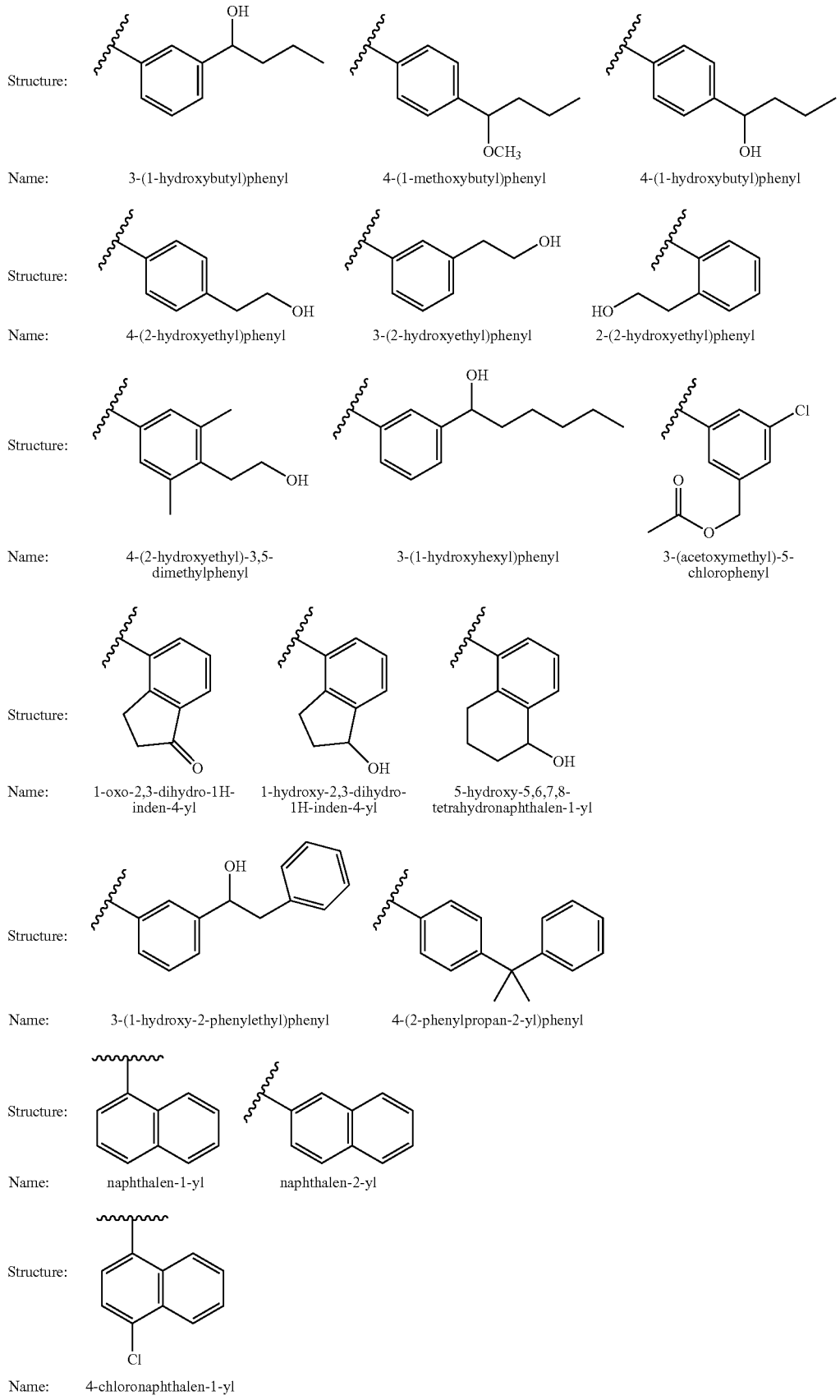

-continued

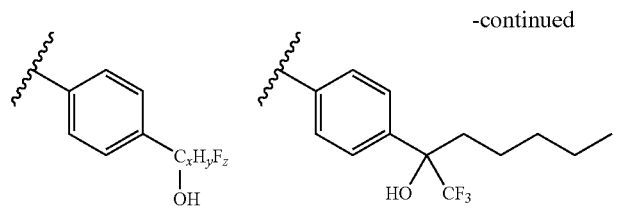

In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

The term aromatic refers to the meaning commonly understood in the art, i.e. it refers to an unsaturated, fully conjugated ring having 4N+2 ring electrons (e.g. 2, 6, 10, etc.) Thus, phenyl, pyridinyl, thienyl, furyl, and the like are aromatic. Aryl is a moiety that is aromatic.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

Unless otherwise indicated, reference to a compound should be construed broadly to include pharmaceutically acceptable salts, tautomers, and prodrugs of the depicted structure.

Unless stereochemistry is explicitly depicted, a structure is intended to include every possible stereoisomer, both pure or in any possible mixture. In particular, compounds having the stereochemistry indicated in the structures below are contemplated.

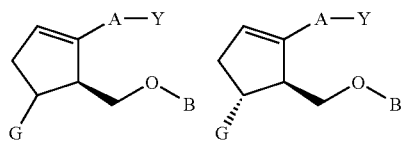

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer." Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition.

Hypothetical useful compounds are depicted below.

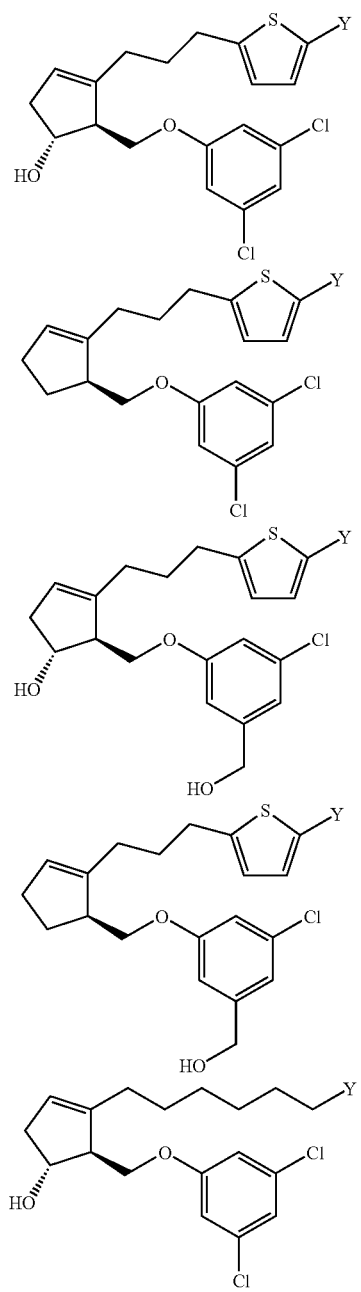

-continued
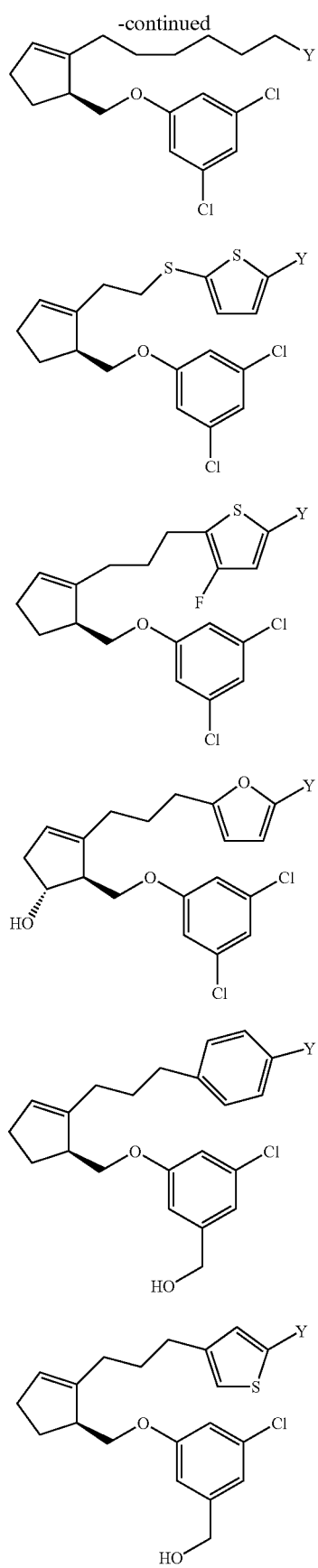
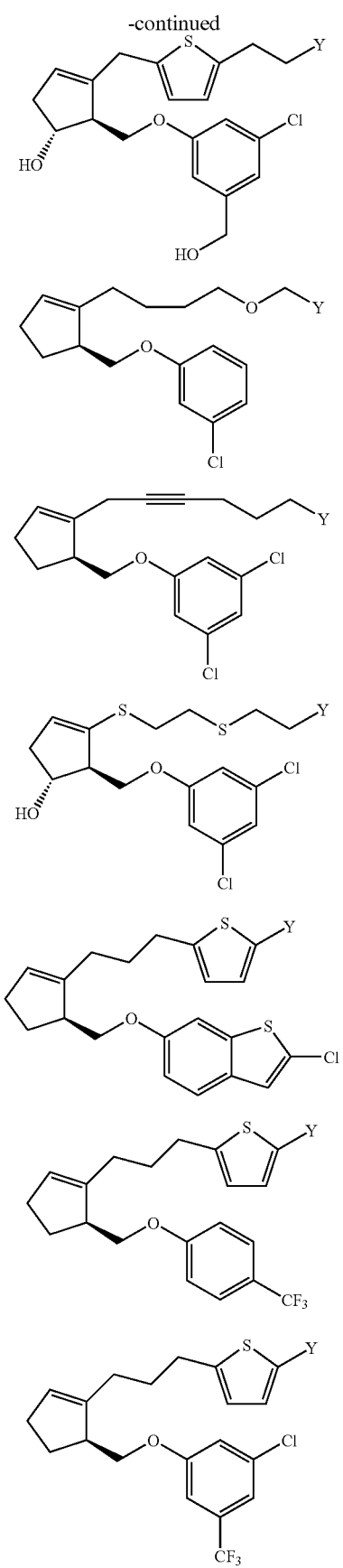

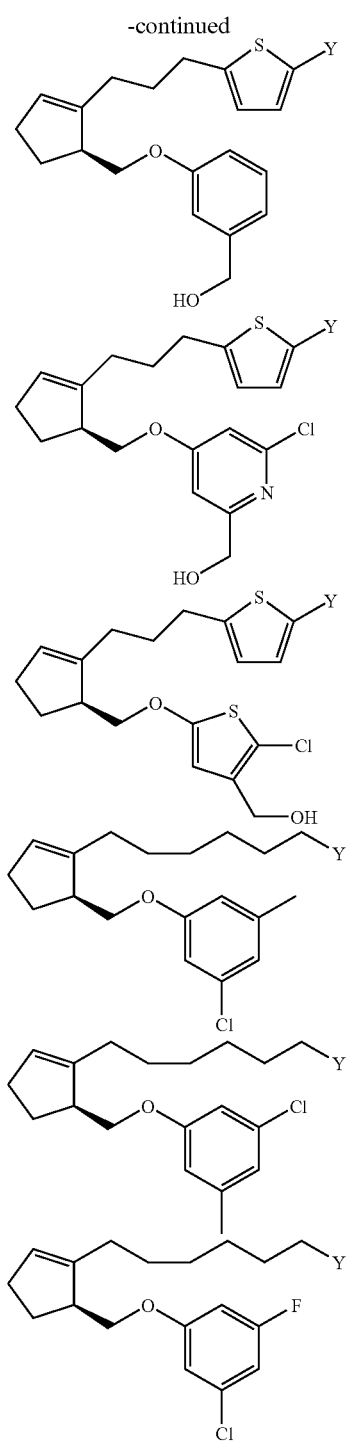

The compounds disclosed herein are useful in the manufacture of a medicament for the treatment of glaucoma or ocular hypertension in a mammal.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiological acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without anti oxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

Synthetic Methods

Scheme 1

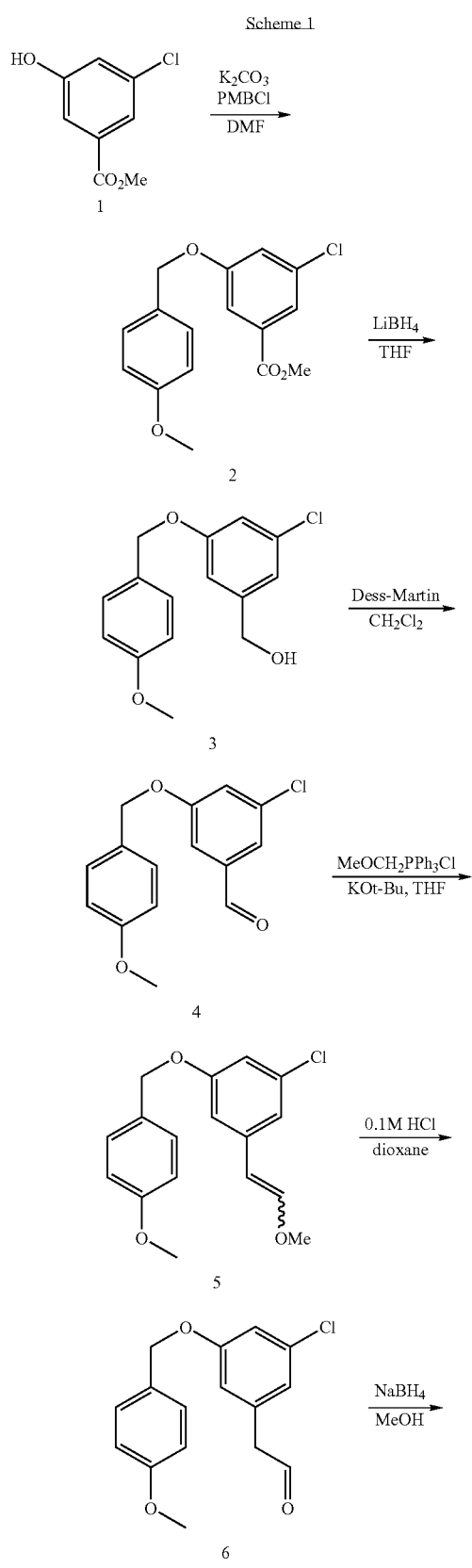

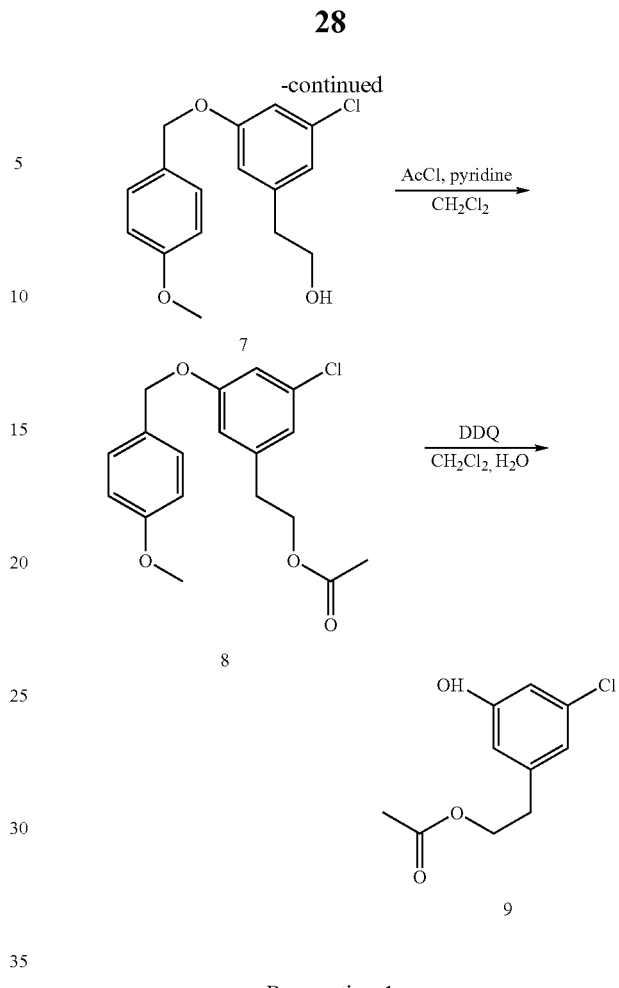

Preparation 1

3-chloro-5-hydroxyphenethyl acetate (9, Scheme 1)

Step 1. Protection of Phenol 1 to Give Ether 2

Potassium carbonate (4.3 g, 31.1 mmol) and 4-methoxybenzyl chloride (2.02 mL, 14.9 mmol) were added to a solution of phenol 1 (see U.S. Provisional Patent Application No. 60/757,696, filed Jan. 10, 2006, incorporated by reference herein, 2.30 g, 12.3 mmol) in DMF (100 mL). The mixture was heated at 100° C. After 3 hours the mixture was allowed to cool to room temperature and then partitioned between water (150 mL) and EtOAc (200 mL). The phases were separated and the organic phase was washed with additional water (100 mL) and brine (50 mL). The organic phase was then dried ($MgSO_4$), filtered and concentrated in vacuo. Purification of the residue by flash column chromatography on silica gel (20% EtOAc/hexane) afforded 3.25 g (86%) of ether 2.

Step 2. Reduction of 2 to Give 3

A solution of ester 2 (3.25 g, 10.6 mmol) in THF (17 mL) was added via syringe to a solution of $LiBH_4$ (0.346 g, 15.9 mmol) in THF (5 mL) at 0° C. The mixture was heated at 80° C. overnight. The reaction mixture was allowed to cool to room temperature, quenched with water, diluted with 5% aqueous citric acid (100 mL) and extracted with EtOAc (75 mL). The organic phase was dried ($MgSO_4$), filtered and concentrated in vacuo. Purification of the crude residue by flash column chromatography on silica gel (30% EtOAc/hexane) afforded 2.91 g (99%) of alcohol 3.

Step 3. Oxidation of 3 to Give 4

A solution of alcohol 3 (2.50 g, 8.97 mmol) in CH$_2$Cl$_2$ (125 mL) was added to a solution of Dess-Martin periodinane (4.57 g, 10.8 mmol) in CH$_2$Cl$_2$ (125 mL). After 2 hours at room temperature the reaction was partitioned between water (500 mL) and CH$_2$Cl$_2$ (300 mL). The phases were separated and the aqueous phase was extracted with CH$_2$Cl$_2$ (2×250 mL). The combined organic phase was washed with brine (200 mL) then dried (MgSO$_4$), filtered and concentrated in vacuo. Purification of the crude residue by flash column chromatography on silica gel (30% EtOAc/hexane) afforded 2.42 g (97%) of aldehyde 4.

Step 4. Wittig Reaction of 4 to Give 5

Potassium tert-butoxide (2.54 g, 22.6 mmol) was added to a solution of methoxymethyltriphenylphosphonium chloride (3.72 g, 10.8 mmol) in THF (60 mL) at 0° C. After 30 minutes at 0° C., a solution of aldehyde 4 (2.5 g, 9.03 mmol) in THF (30 mL) was added. The reaction mixture was allowed to warm to room temperature and stirred overnight. The reaction was quenched at 0° C. by the slow addition of H$_2$O then was partitioned between 10% aqueous HCl (95 mL) and EtOAc (100 mL). The phases were separated and the aqueous phase was extracted with EtOAc (2×50 mL). The combined organic phase was washed with brine (20 mL) then dried (MgSO$_4$), filtered and concentrated in vacuo. Purification of the crude residue by flash column chromatography on silica gel (40% EtOAc/hexane) afforded 2.70 g (98%) of enol ether 5.

Step 5. Hydrolysis of 5 to Give 6

M aqueous HCl (2.84 mL, 0.28 mmol) was added to a solution of enol ether 5 (2.70 g, 8.86 mmol) in dioxane (90 mL). After 1 hour at room temperature, the mixture was heated at 60° C. for 2.5 hours then cooled to room temperature. The reaction mixture was partitioned between saturated aqueous NaHCO$_3$ (300 mL) and CH$_2$Cl$_2$ (300 mL). The phases were separated and the aqueous phase was extracted with CH$_2$Cl$_2$ (2×300 mL). The combined organic phase was washed with H$_2$O and brine then dried (MgSO$_4$), filtered and concentrated in vacuo. Purification of the crude residue by flash column chromatography on silica gel (30% EtOAc/hexane) afforded 812 mg (32%) of aldehyde 6.

Step 6. Reduction of 6 to Give 7

Sodium borohydride (159 mg, 4.20 mmol) was added to a solution of aldehyde 6 (812 mg, 2.79 mmol) in MeOH (34 mL) at 0° C. The mixture was allowed to warm to room temperature. After 20 minutes at room temperature, the reaction was cooled to 0° C. and quenched by the slow addition of water. The mixture was then diluted with water (200 mL) and extracted with EtOAc (2×300 mL). The combined organic phase was washed with brine, dried (MgSO$_4$), filtered and concentrated in vacuo. Purification of the crude residue by flash column chromatography on silica gel (50% EtOAc/hexane) afforded 816 mg (99%) of alcohol 7.

Step 7. Protection of 7 to Give 8

Pyridine (247 μL, 3.05 mmol) and acetyl chloride (216 μL, 3.04 mmol) were added sequentially to a solution of alcohol 7 (816 mg, 2.79 mmol) in CH$_2$Cl$_2$ (15 mL). After 5 min, the reaction mixture was partitioned between saturated aqueous NaHCO$_3$ (150 mL) and CH$_2$Cl$_2$ (150 mL). The phases were separated and the aqueous phase was extracted with CH$_2$Cl$_2$ (2×150 mL). The combined organic phases were washed with brine (150 mL), dried (MgSO$_4$), filtered and concentrated in vacuo. Purification of the crude residue by flash column chromatography on silica gel (10% EtOAc/hexane) afforded 850 mg (91%) of acetate 8.

Step 8. Deprotection of 8 to Give 9

2,3-Dichloro-5,6-dicyano-1,4-benzoquinone (DDQ, 814 mg, 3.59 mmol) was added to a mixture of ether 8 (400 mg, 1.19 mmol) in CH$_2$Cl$_2$ (9 mL) and H$_2$O (0.45 mL) at 0° C. After 1 hour at 0° C. the reaction was allowed to warm to room temperature. After 4 hours at room temperature, the reaction was quenched with saturated aqueous NaHCO$_3$ (100 mL). The mixture was extracted with CH$_2$Cl$_2$ (3×100 mL). The combined extracts were washed with water and brine then dried (MgSO$_4$), filtered and concentrated in vacuo. Purification of the residue by flash column chromatography on silica gel (30% EtOAc/hexane) afforded 80 mg (31%) of the title compound (9).

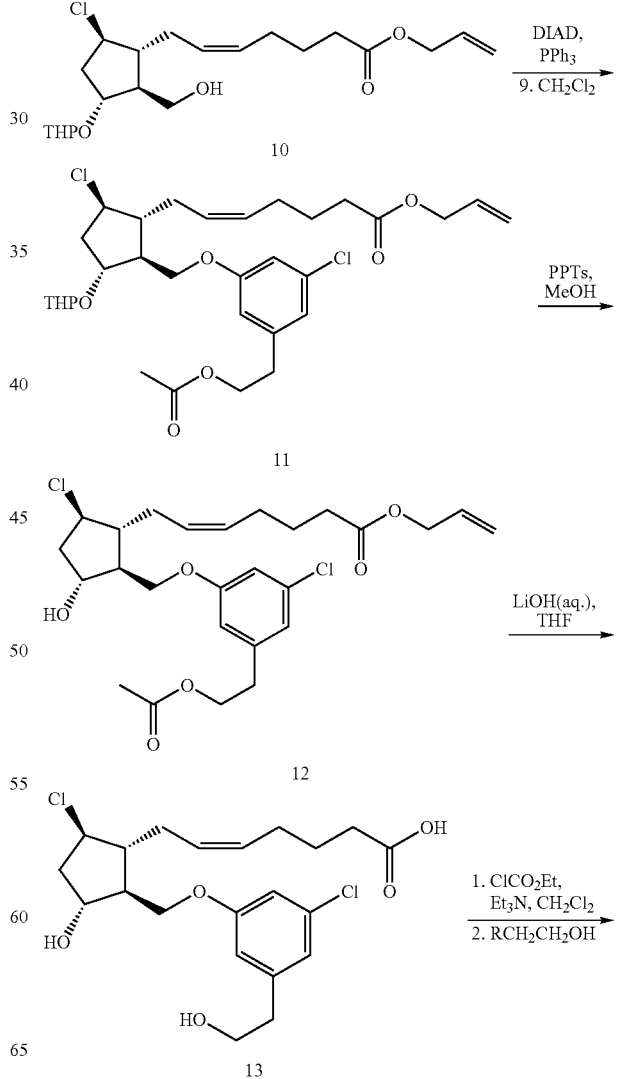

Scheme 2

-continued

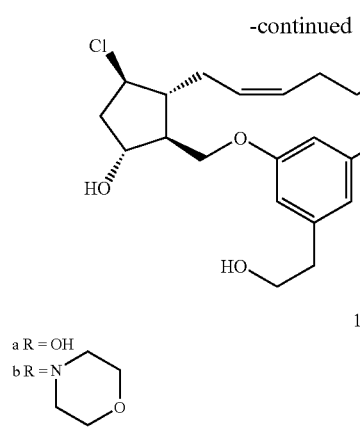

14
a R = OH
b R = N⌐morpholine

EXAMPLE 1

Step 1. Mitsunobu Reaction of 9 and 10 to Give 11

Triphenylphosphine (98 mg, 0.37 mmol) and diisopropyl azodicarboxylate (DIAD, 58 L, 0.30 mmol) were added sequentially to a solution of alcohol 10 (see U.S. Provisional Patent Application No. 60/757,696, filed Jan. 10, 2006; 100 mg, 0.25 mmol) and phenol 9 (preparation 1, 80 mg, 0.37 mmol) in $CH_2Cl_2$ (1.0 mL). After stirring 18 hours at room temperature, the reaction mixture was partitioned between saturated aqueous $NaHCO_3$ (20 mL) and $CH_2Cl_2$ (15 mL). The phases were separated and the aqueous phase was extracted with $CH_2Cl_2$ (2×20 mL). The combined organic phase was washed with brine (15 mL), dried ($MgSO_4$), filtered and concentrated in vacuo. Purification of the residue by flash column chromatography on silica gel (20% EtOAc/hexane) afforded 108 mg (72%) of aryl ether 11.

Step 2: Deprotection of 11 to Give 12

Pyridinium p-toluenesulfonate (PPTs, 4.7 mg, 0.019 mmol) was added to a solution of 11 (108 mg, 0.18 mmol) in methanol (2.0 mL) at room temperature under nitrogen. The solution was heated at 40° C. for 5 h, then cooled and concentrated in vacuo. Purification of the crude residue by flash column chromatography on silica gel (50% EtOAc/hexane) afforded 53 mg (57%) of alcohol 12.

Step 3: Hydrolysis of 12 to Give 13

Lithium hydroxide (0.15 mL of a 1.0 M aqueous solution, 0.15 mmol) was added to a solution of ester 12(13 mg, 0.025 mmol) in THF (0.13 mL). After 2 hours room temperature, the reaction was partitioned between 10% aqueous HCl (3 mL) and EtOAc (7 mL). The phases were separated and the aqueous phase was extracted with EtOAc (2×7 mL). The combined organic phase was washed with brine, dried ($MgSO_4$), filtered and concentrated in vacuo to afford 11 mg (quant.) of compound 13.

Step 4: Conversion of 13 to Give 14a or 14b

Triethylamine and ethyl chloroformate are added sequentially to a solution of compound 13 in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 14a.

Triethylamine and ethyl chloroformate are added sequentially to a solution of compound 1 in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 14b.

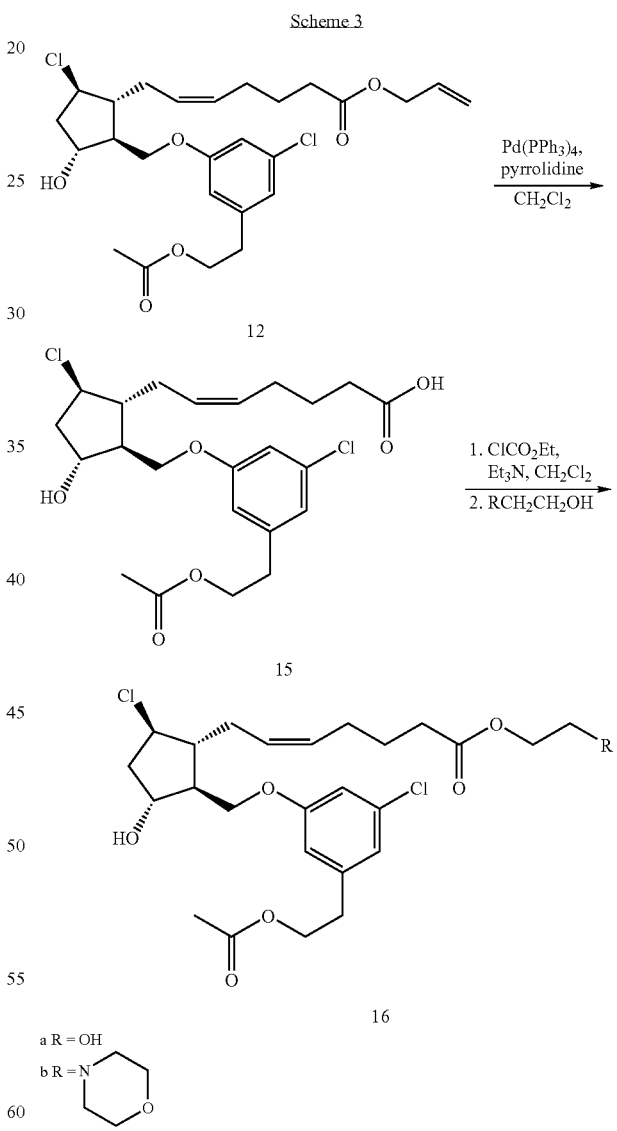

Scheme 3

16
a R = OH
b R = N⌐morpholine

EXAMPLE 2

Tetrakis(triphenylphosphine)palladium(0) (20 mg, 0.017 mmol) and pyrrolidine (14 μL, 0.17 mmol) were added sequentially to a solution of allyl ester 12 (30 mg, 0.058 mmol) in CH$_2$Cl$_2$ (1.0 mL). After 5 min the reaction mixture was partitioned between 1.0 M aqueous HCl (5 mL) and CH$_2$Cl$_2$ (15 mL). The phases were separated and the aqueous phase was extracted with CH$_2$Cl$_2$ (2×10 mL). The combined extracts were washed with brine (10 mL), dried (MgSO$_4$), filtered and concentrated in vacuo. Purification of the crude residue by flash column chromatography on silica gel (60% EtOAc/hexane) afforded 9 mg (33%) of compound 15.

Compound 15 can be converted to compounds 16a or 16b according to the steps outlined in Example 1, Step 4.

Scheme 4

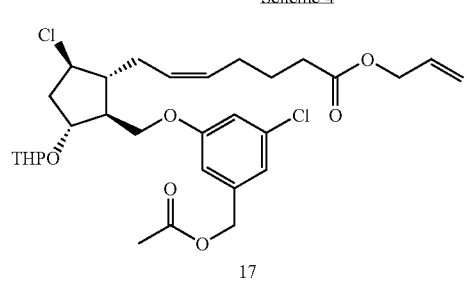

17

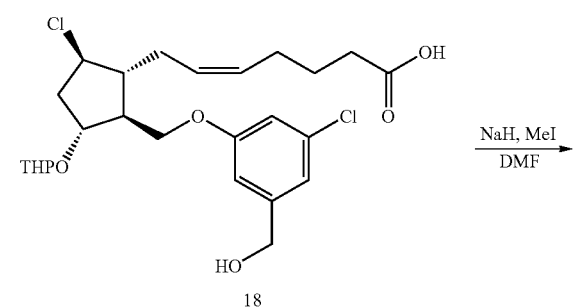

18

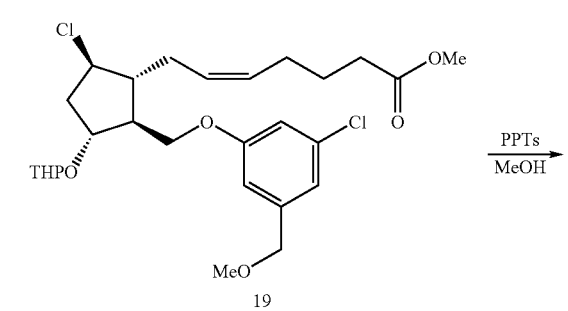

19

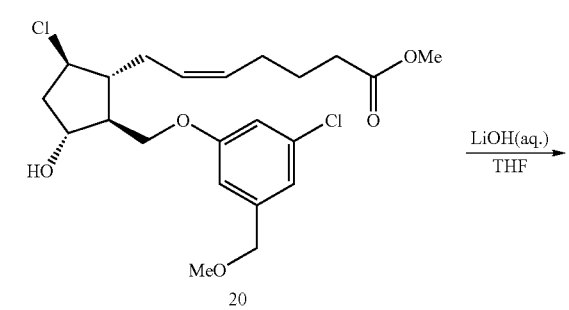

20

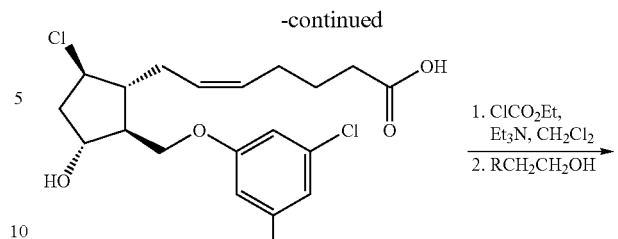

21

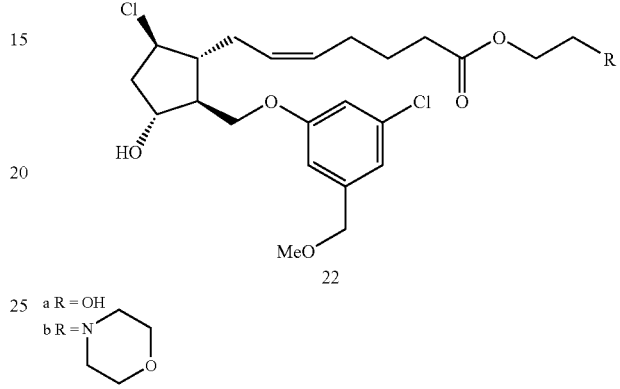

22 a R = OH
b R = N⟨morpholine⟩

Step 1. Hydrolysis of 17 to Give 18

Ester 17 (see U.S. Provisional Patent Application No. 60/757,696, filed Jan. 10, 2006; 200 mg, 0.343 mmol) was converted into 140 mg (57%) of hydroxy-acid 18 in accordance with the procedure of Example 1, step 3.

Step 2. Dimethylation of 18 to Give 19

A solution of hydroxy-acid 18 (54 mg, 0.11 mmol) in DMF (0.5 mL) was added to a suspension of sodium hydride (11 mg of a 60 wt. % suspension, 0.28 mmol) in DMF (0.5 mL). Iodomethane (67 μL, 1.08 mmol) was then added. The reaction mixture was partitioned between water (5 mL) and EtOAc (10 mL). The phases were separated and the aqueous phase was extracted with EtOAc (2×10 mL). The combined extracts were washed with brine (10 mL), dried (MgSO$_4$), filtered and concentrated in vacuo. Purification of the crude residue by flash column chromatography on silica gel (hexanes→EtOAc, gradient) afforded 50 mg (88%) of 19.

Step 3. Deprotection of 19 to Give 20

Acetal 19 (50 mg, 0.094 mmol) was converted into 23 mg (55%) of alcohol 20 in accordance with the procedure of Example 1, step 2.

Step 4. Hydrolysis of 20 to Give 21

Ester 20 (23 mg, 0.052 mmol) was converted into 13 mg (58%) of compound in accordance with the procedure of Example 1, step 3.

Step 5. Conversion of Compound 21 to Give 22a or 22b

Compound 21 can be converted to compounds 22a or 22b according to the steps outlined in Example 1, Step 4.

Scheme 5

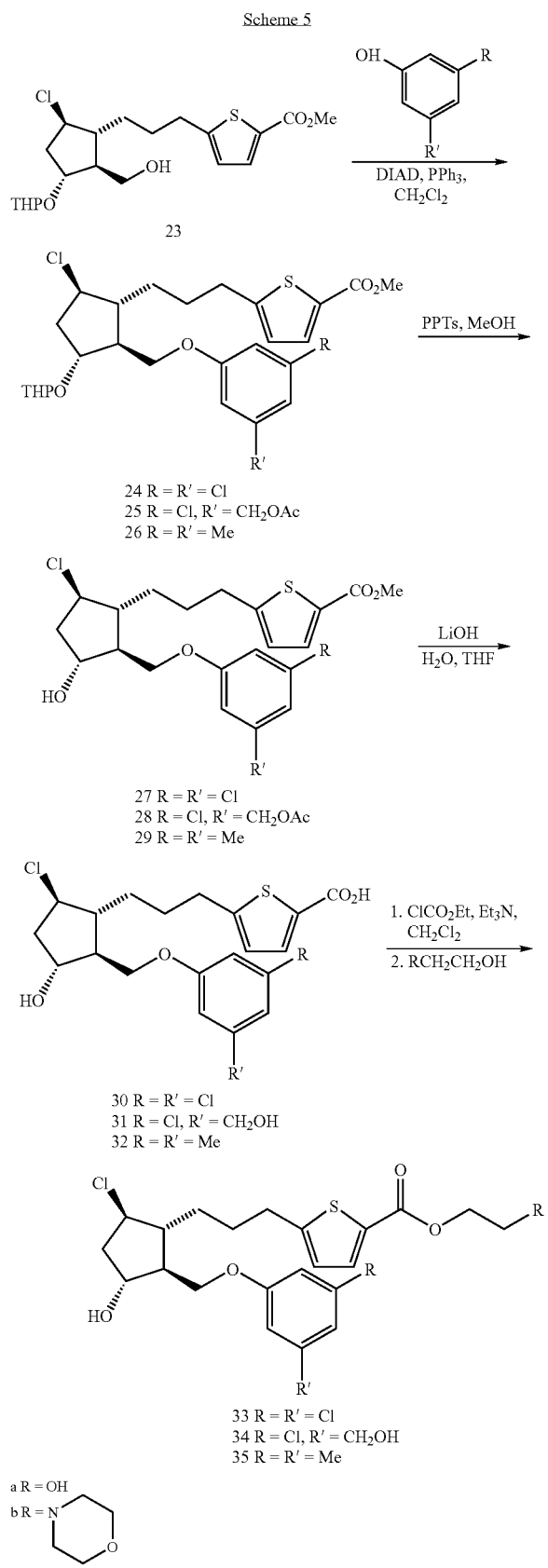

EXAMPLE 4

Step 1. Mitsunobu Reaction of 23 to Give 24

Triphenylphosphine (38 mg, 0.14 mmol) and DIAD (23 µL, 0.12 mmol) were added to a solution of alcohol 23 (see U.S. Provisional Patent Application No. 60/805,285, filed Jun. 20, 2006, incorporated by reference herein; 40 mg, 0.096 mmol) and 3,5-dichlorophenol (23 mg, 0.14 mmol) in $CH_2Cl_2$ (1.0 mL). After stirring 18 hours at room temperature, the mixture was partitioned between $CH_2Cl_2$ (10 mL) and saturated aqueous $NaHCO_3$ (10 mL). The phases were separated and the aqueous phase was extracted with $CH_2Cl_2$ (2×10 mL). The combined organic phase was washed with brine (10 mL), dried ($MgSO_4$), filtered and concentrated in vacuo. Purification of the residue by flash column chromatography on silica gel (hexane→EtOAc, gradient) afforded 20 mg (37%) of 24.

Step 2. Deprotection of 24 to Give 27

Pyridinium p-toluenesulfonate (PPTs, 1 mg, 0.004 mmol) was added to a solution of 24 (20 mg, 0.036 mmol) in methanol (0.35 mL) at room temperature. The solution was heated at 40° C. overnight, then cooled and concentrated in vacuo. Purification of the crude residue by flash column chromatography on silica gel (hexane→EtOAc, gradient) afforded 10 mg (59%) of 27.

Step 3. Hydrolysis of 27 to Give 30

Ester 27 (10 mg, 0.021 mmol) was converted into 3 mg (31%) of compound 30 in accordance with the procedure of Example 1, step 3 with the following modifications: the reaction was stirred for 18 hours at room temperature, and the crude product was purified by flash column chromatography on silica gel (10% $MeOH/CH_2Cl_2$).

Step 4. Conversion of Compound 30 to Give 33a or 33b

Compound 30 can be converted to compounds 33a or 33b according to the steps outlined in Example 1, Step 4.

EXAMPLE 5

Ester 28 (see U.S. Provisional Patent Application No. 60/805,285, filed Jun. 20, 2006; 30 mg, 0.058 mmol) was converted into 13 mg (49%) of compound 31 in accordance with the procedure of Example 4, step 3. Compound 31 can be converted to compounds 34a or 34b according to the steps outlined in Example 1, Step 4.

EXAMPLE 6

Step 1. Mitsunobu Reaction of 20 to Give 26

Triphenylphosphine (47 mg, 0.18 mmol) and DIAD (27 µL, 0.14 mmol) were added to a solution of alcohol 23 (see U.S. Provisional Patent Application No. 60/805,285, filed Jun. 20, 2006; 50 mg, 0.12 mmol) and 3,5-dimethylphenol (17 mg, 0.14 mmol) in $CH_2Cl_2$ (0.6 mL). After stirring 18 hours at room temperature, the mixture was partitioned between $CH_2Cl_2$ (10 mL) and saturated aqueous $NaHCO_3$ (10 mL). The phases were separated and the aqueous phase was extracted with $CH_2Cl_2$ (2×10 mL). The combined organic phase was washed with brine (10 mL), dried ($MgSO_4$), filtered and concentrated in vacuo. Purification of the residue by flash column chromatography on silica gel (hexane→EtOAc, gradient) afforded 53 mg (85%) of 26.

Step 2. Deprotection of 26 to Give 29

Acetal 26 (53 mg, 0.10 mmol) was converted into 37 mg (83%) of alcohol 29 in accordance with the procedure of Example 4, step 2

Step 3. Hydrolysis of 29 to Give 32

Ester 29 (37 mg, 0.085 mmol) was converted into 15 mg (42%) of compound 32 in accordance with the procedure of Example 1, step 3 with the following modifications: the reaction was stirred for 18 hours at 40° C., and the crude product was purified by flash column chromatography on silica gel (10% MeOH/CH$_2$Cl$_2$).

Step 4. Conversion of Compound 32 to give 35a or 35b

Compound 32 can be converted to compounds 35a or 35b according to the steps outlined in Example 1, Step 4.

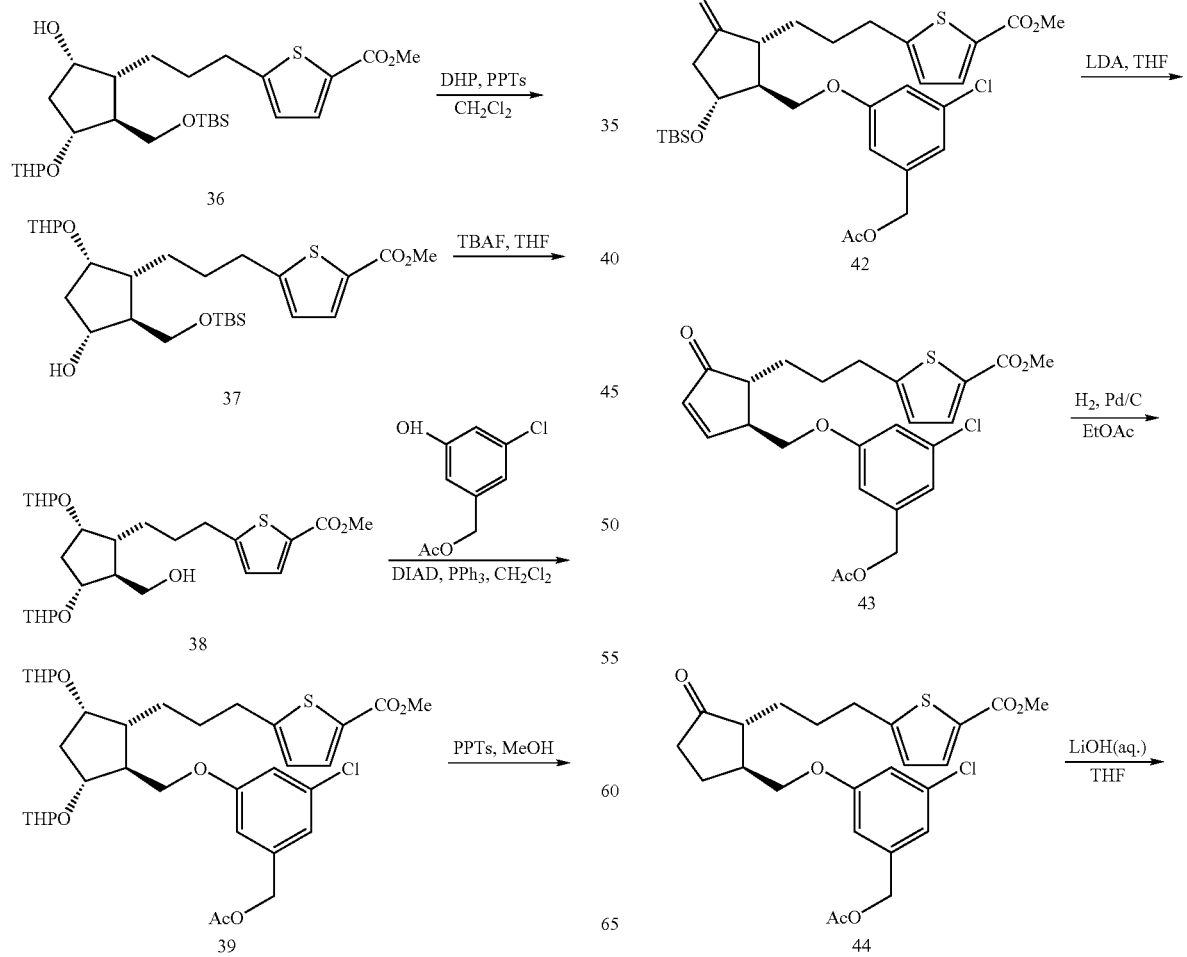

-continued

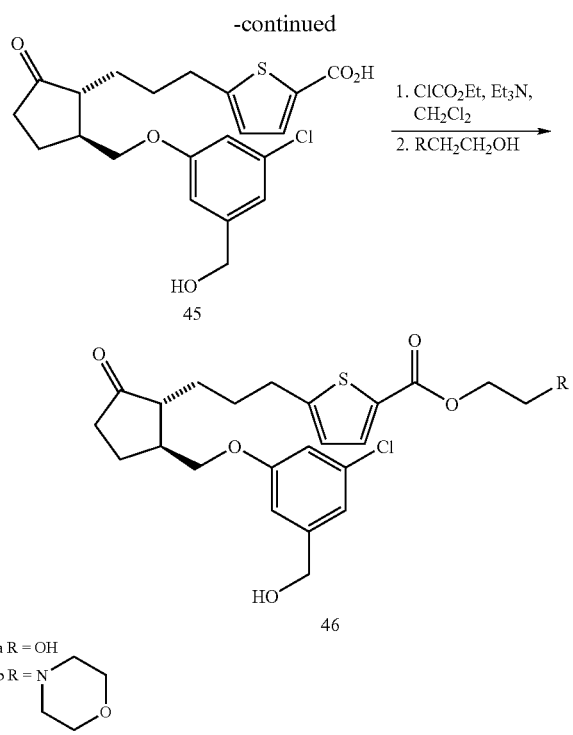

a R = OH
b R = N(morpholine)

EXAMPLE 7

Step 1. Protection of 36 to Give 37

Dihydropyran (391 μL, 4.29 mmol) and PPTs (50 mg, 0.20 mmol) were added to a solution of alcohol 36 (see U.S. Provisional Patent Application No. 60/805,285, filed Jun. 20, 2006; 550 mg, 1.07 mmol) in $CH_2Cl_2$ (3.0 mL). The reaction mixture was heated at 40° C. overnight, then cooled and concentrated in vacuo. Purification of the crude residue by flash column chromatography on silica gel (hexane→EtOAc, gradient) afforded 550 mg (86%) of 37.

Step 2. Desilylation of 37 to Give 38

Tetrabutylammonium fluoride (2.51 mL of a 1.0 M THF solution, 2.51 mmol) was added to a solution of 37 (500 mg, 0.84 mmol) in THF (7.6 mL). After 18 hours at room temperature, the reaction mixture was partitioned between water (10 mL) and EtOAc (20 mL). The phases were separated and the aqueous phase was extracted with EtOAc (2×10 mL). The combined extracts were washed with brine then dried ($MgSO_4$), filtered and concentrated in vacuo. Purification of the crude residue by flash column chromatography on silica gel (hexane→EtOAc, gradient) afforded 393 mg (97%) of 38.

Step 3. Mitsunobu of 38 to Give 39

Alcohol 38 (437 mg, 0.91 mmol) and 3-chloro-5-hydroxybenzyl acetate (see U.S. Provisional Patent Application No. 60/757,696, filed Jan. 10, 2006; 218 mg, 1.09 mmol) were converted into 350 mg (58%) of aryl ether 39 in accordance with the procedure of Example 6, step 1.

Step 4. Deprotection of 39 to Give 40

Bis-acetal 39 (350 mg, 0.53 mmol) was converted into 150 mg (57%) of diol 40 in accordance with the procedure of Example 4, step 2.

Step 5. Monosilylation of 40 to Give 41

Triethylamine (63 μL, 0.45 mmol), dimethylaminopyridine (7 mg, 0.057 mmol), and tert-butyldimethylsilyl chloride (50 mg, 0.33 mmol) were sequentially added to a solution of 40 (150 mg, 0.30 mmol) in $CH_2Cl_2$ (1.5 mL). After stirring 18 hours at room temperature, the mixture was partitioned between $CH_2Cl_2$ (10 mL) and saturated aqueous $NaHCO_3$ (5 mL). The phases were separated and the aqueous phase was extracted with $CH_2Cl_2$ (2×10 mL). The combined organic phase was washed with brine (10 mL), dried ($MgSO_4$), filtered and concentrated in vacuo. Purification of the residue by flash column chromatography on silica gel (hexane→EtOAc, gradient) afforded 90 mg (49%) of 41.

Step 6. Oxidation of 41 to Give 42

Dess-Martin periodinane (75 mg, 0.18 mmol) was added to a solution of 41 (90 mg, 0.15 mmol) in $CH_2Cl_2$ (7.35 mL) at 0° C. and the mixture was allowed to warm to room temperature. After 2 hours at room temperature, the mixture was partitioned between $CH_2Cl_2$ (10 mL) and water (10 mL). The phases were separated and the aqueous phase was extracted with $CH_2Cl_2$ (2×10 mL). The combined organic phase was washed with brine (5 mL), dried ($MgSO_4$), filtered and concentrated in vacuo. Purification of the residue by flash column chromatography on silica gel (hexane→EtOAc, gradient) afforded 80 mg (89%) of ketone 42.

Step 7. Elimination of 42 to Give 43

A solution of lithium diisopropylamide (0.41 mL of a 2.0 M solution in heptane-THF-ethylbenzene, 0.82 mmol) was added to a solution of 42 (80 mg, 0.13 mmol) in THF (2.3 mL) at −78° C. After 90 minutes at −78° C., the mixture was allowed to warm to room temperature. After 15 minutes at room temperature, the reaction was quenched by the addition of 0.1 N aqueous HCl (15 mL), and extracted with EtOAc (3×20 mL). The combined extracts were washed with brine, dried ($MgSO_4$), filtered and concentrated in vacuo. Purification of the residue by flash column chromatography on silica gel (hexane→EtOAc, gradient) afforded 40 mg (64%) of enone 43.

Step 8. Hydrogenation of 43 to Give 44

Palladium on carbon (10 wt. %, 8 mg) was added to a solution of enone 43 (40 mg, 0.084 mmol) in EtOAc (1.6 mL). A hydrogen atmosphere was established by evacuating and refilling with hydrogen (5×) and the reaction mixture was stirred under a balloon of hydrogen for 18 hours. The reaction mixture was filtered through celite, washing with EtOAc, and the filtrate was concentrated in vacuo to afford 31 mg (77%) of saturated ketone 44.

Step 9. Hydrolysis of 44 to Give 45

Ester 44 (5 mg, 0.010 mmol) was converted into 3.5 mg (79%) compound 45 in accordance with the procedure of Example 4, step 3.

Step 10. Conversion of Compound 45 to Give 46a or 46b

Compound 45 can be converted to compounds 46a or 46b according to the steps outlined in Example 1, Step 4.

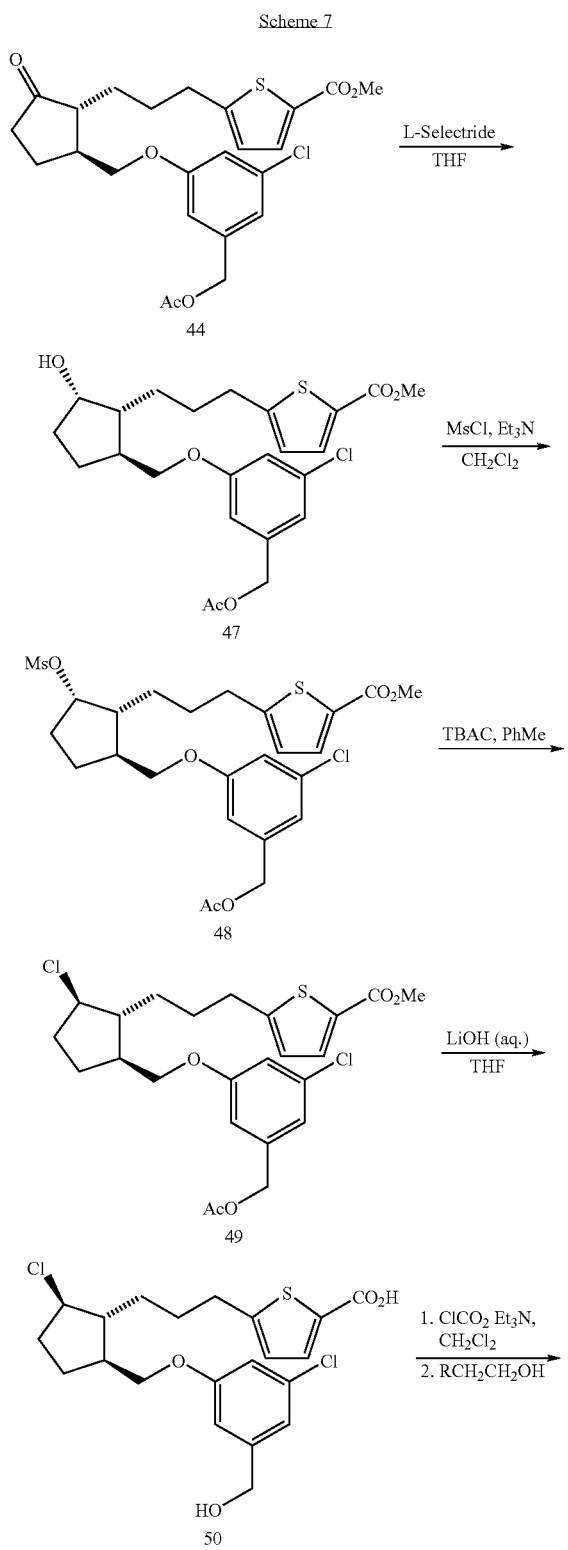

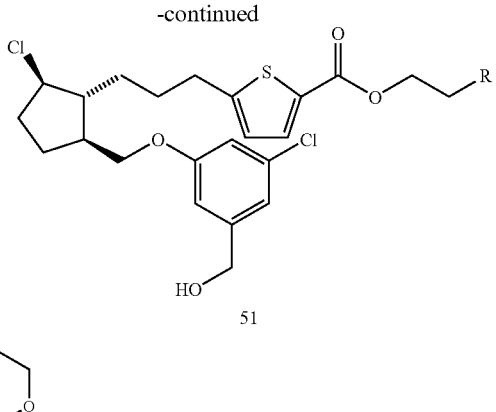

a R = OH
b R = N(morpholine)

EXAMPLE 8

Step 1. Reduction of 44 to Give 47

A solution of L-selectride (74 μL of a 1.0 M solution in THF, 0.074 mmol) was added to a solution of 44 (26 mg, 0.054 mmol) in THF (1.8 mL) at −78° C. After 1 hour at −78° C., additional L-selectride (108 μL, 0.108 mmol) was added. After 5 hours at −78° C., the reaction was quenched by the addition of 3% aqueous $H_2O_2$ (1.5 mL) and the mixture was allowed to warm to room temperature. Water (5 mL) was added and the mixture was extracted with EtOAc (2×10 mL). The combined extracts were dried ($MgSO_4$), filtered and concentrated in vacuo. Purification of the residue by flash column chromatography on silica gel (hexane→EtOAc, gradient) afforded 13 mg (50%) of alcohol 47.

Step 2. Mesylation of 47 to Give 48

Triethylamine (5.6 μL, 0.040 mmol) and methanesulfonyl chloride (2.6 μL, 0.033 mmol) were added sequentially to a solution of 47 (13 mg, 0.027 mmol) in $CH_2Cl_2$ (0.2 mL) at 0° C., and reaction was allowed to warm to room temperature. After 18 hours at room temperature, saturated aqueous $NaHCO_3$ (5 mL) was added and the mixture was extracted with $CH_2Cl_2$ (3×5 mL). The combined extracts were washed with brine (2 mL), dried ($MgSO_4$), filtered and concentrated in vacuo to afford 15 mg (99%) of mesylate 48.

Step 3. Conversion of 48 to Chloride 49

Tetrabutylammonium chloride (38 mg, 0.14 mmol) was added to a solution of 48 (15 mg, 0.027 mmol) in toluene (0.27 mL). The reaction mixture was heated at 50° C. for 18 hours. The cooled mixture was diluted with brine (10 mL) and extracted with EtOAc (3×25 mL). The combined organic extracts were dried ($MgSO_4$), filtered and concentrated in vacuo. Purification of the crude residue by flash column chromatography on silica gel (hexane→EtOAc, gradient) afforded 5 mg (37%) of chloride 49.

Step 4. Hydrolysis of 49 to Give 50

Ester 49 (5 mg, 0.010 mmol) was converted into 1 mg (23%) of compound 50 in accordance with the procedure of Example 4, step 3.

Step 5. Conversion of Compound 50 to Give 51a or 51b

Compound 50 can be converted to compounds 51a or 51b according to the steps outlined in Example 1, Step 4.

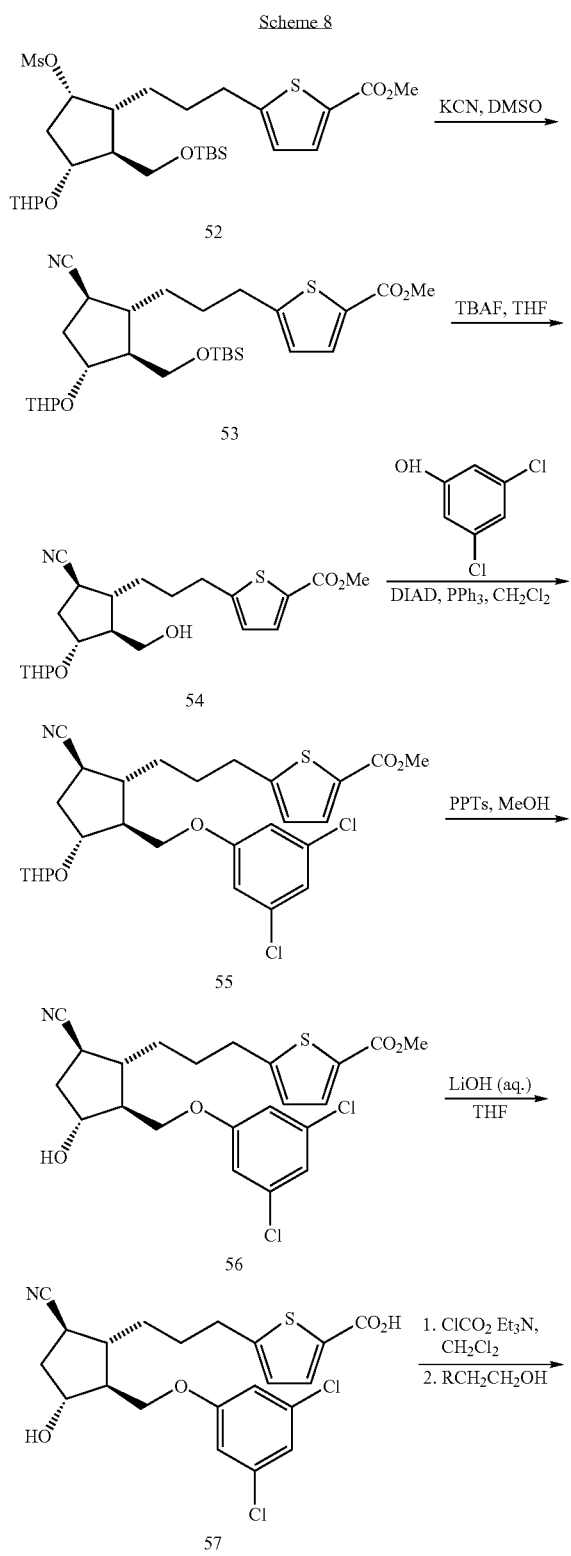

Scheme 8

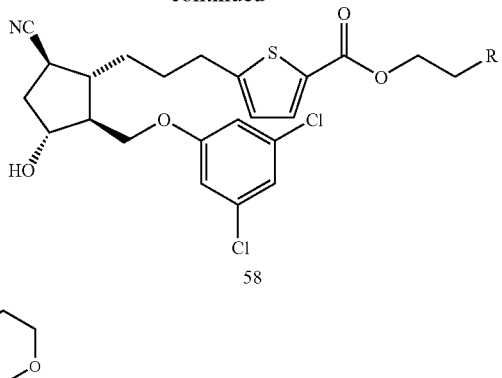

a R = OH
b R = N(morpholine)

EXAMPLE 9

Step 1. Conversion of 52 to Give Nitrile 53

Potassium cyanide (569 mg, 8.74 mmol) was added to a solution of mesylate 52 (see U.S. Provisional Patent Application No. 60/805,285, filed Jun. 20, 2006; 2.10 g, 3.55 mmol) in DMSO (97 mL). The mixture was heated at 65° C. for 18 hours then cooled to room temperature. The mixture was diluted with water (100 mL) and brine (100 mL) and extracted with CH$_2$Cl$_2$ (3×200 mL). The combined organic phase was dried (MgSO$_4$) filtered and concentrated in vacuo. Purification of the residue by flash column chromatography on silica gel (hexane→EtOAc, gradient) afforded 270 mg (15%) of nitrile 53.

Step 2. Desilylation of 53 to Give 54

Silyl ether 53 (270 mg, 0.52 mmol) was converted into 150 mg (71%) of alcohol 54 in accordance with the procedure of Example 7, step 2.

Step 3. Mitsunobu of 54 to Give 55

Alcohol 54 (50 mg, 0.12 mmol) and 3,5-dichlorophenol (24 mg, 0.15 mmol) were converted into 50 mg (74%) of aryl ether 55 in accordance with the procedure of Example 6, step 1.

Step 4. Deprotection of 55 to Give 56

Acetal 55 (50 mg, 0.090 mmol) was converted into 20 mg (47%) of alcohol 56 in accordance with the procedure of Example 4, step 2.

Step 5. Hydrolysis of 56 to Give 57

Ester 56 (15 mg, 0.032 mmol) was converted into 8 mg (55%) of compound 57 in accordance with the procedure of Example 1, step 3 with the following modifications: the concentration was 0.4 M in THF, the reaction was stirred for 18 hours at 40° C., and the crude product was purified by flash column chromatography on silica gel (10% MeOH/CH$_2$Cl$_2$).

Step 6. Conversion of Compound 57 to Give 58a or 58b

Compound 57 can be converted to compounds 58a or 58b according to the steps outlined in Example 1, Step 4.

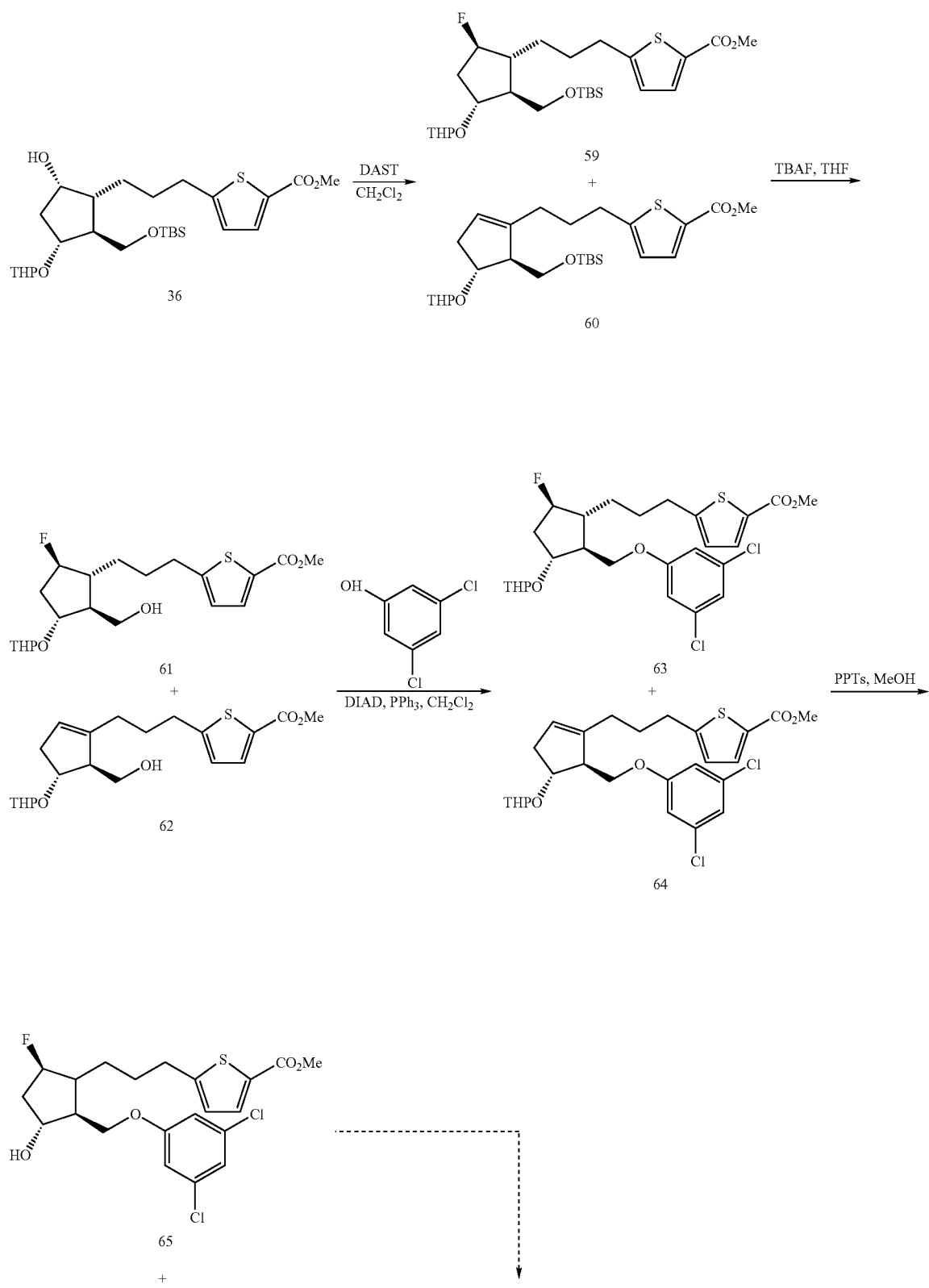

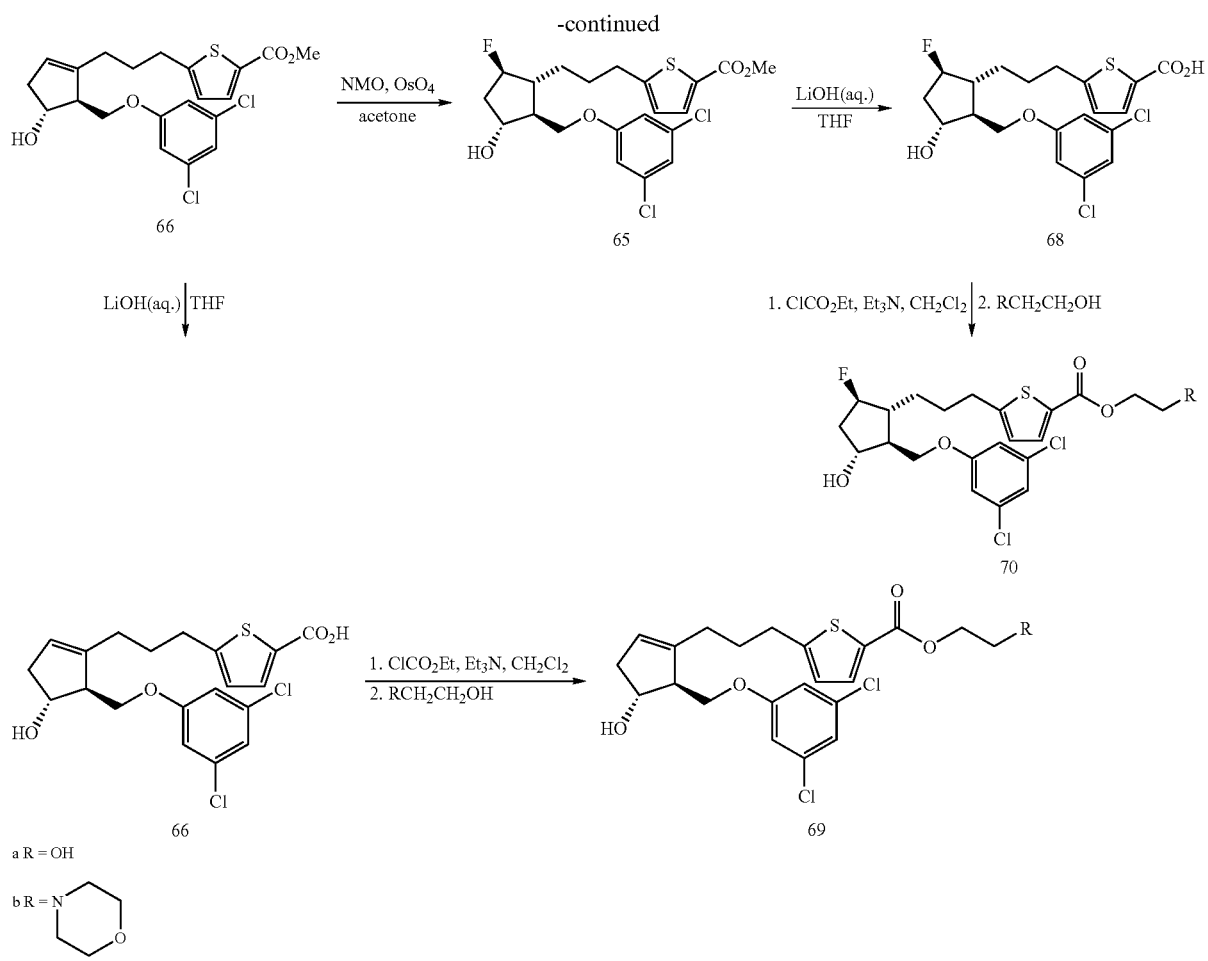

EXAMPLE 10

Step 1. Conversion of 36 to Fluoride 59 and Alkene 60

(Diethylamino)sulfur trifluoride (DAST, 104 μL, 0.79 mmol) was added to a solution of alcohol 36 (see U.S. Provisional Patent Application No. 60/805,285, filed Jun. 20, 2006; 200 mg, 0.39 mmol) in $CH_2Cl_2$ (92 mL) at −78° C. After 30 minutes at room temperature, the reaction was quenched with saturated aqueous $NaHCO_3$ (25 mL). The mixture was diluted with water (25 mL) and extracted with $CH_2Cl_2$ (2×25 mL). The combined organic phase was dried ($MgSO_4$), filtered and concentrated in vacuo. Purification of the residue by flash column chromatography on silica gel (hexane→EtOAc, gradient) afforded 42 mg (~20%) of an inseparable mixture of 59 and 60.

Step 2. Disilylation of 59/60 to 61/62

Silyl ethers 59/60 (42 mg, ~0.08 mmol) were converted into 25 mg (~77%) of inseparable alcohols 61/62 in accordance with the procedure of Example 7, step 2.

Step 3. Mitsunobu of 61/62 to 63/64

Alcohols 61/62 (25 mg, ~0.06 mmol) and 3,5-dichlorophenol (9 mg, 0.055 mmol) were converted into 24 mg (~70%) of inseparable aryl ethers 63/64 in accordance with the procedure of Example 6, step 1.

Step 4. Deprotection of 63/64 to 65 and 66

Acetals 63/64 (24 mg, ~0.45 mmol) were converted into 1 mg (~5%) of hydroxyl alkene 66 and 20 mg (~83%) of a mixture of 65 and 66 in accordance with the procedure of Example 4, step 2.

Step 5. Hydrolysis of 66 to 67

Ester 66 (1 mg, 0.022 mmol) was converted into 1 mg (quant.) of 67 in accordance with the procedure of Example 6, step 3.

Step 6. Conversion of Compound 67 to Give 69a or 69b

Compound 67 can be converted to compounds 69a or 69b according to the steps outlined in Example 1, Step 4.

EXAMPLE 11

Step 1. Oxidation of 65/66 to Afford Pure 65

Osmium tetroxide (160 μL of a 4 wt. % solution in water, 0.026 mmol) was added to a solution of 4-methylmorpholine N-oxide (NMO, 11.4 mg, 0.097 mmol) and the mixture of 65 and 66 (Example 10, step 4, 20 mg, ~0.044 mmol) in acetone (1.1 mL) at 0° C. and the reaction was allowed to warm to room temperature. After 1 h, the reaction was quenched with 5% aqueous $NaHCO_3$ (5 mL) and extracted with EtOAc (3×5 mL). The combined extracts were washed with brine (5 mL), dried ($MgSO_4$), filtered and concentrated in vacuo. Purification of the residue by flash column chromatography on silica gel (hexane→EtOAc, gradient) afforded 5 mg (~24%) of fluoride 65.

Step 2. Hydrolysis of 65 to Give 68

Ester 65 (5 mg, 0.011 mmol) was converted into 2 mg (41%) of compound 68 in accordance with the procedure of Example 6, step 3.

Step 3. Conversion of Compound 68 to Give 70a or 70b

Compound 68 can be converted to compounds 70a or 70b according to the steps outlined in Example 1, Step 4.

IN VIVO EXAMPLES

Compounds 14a, 14b, 16a, 16b. 22a, 22b, 33a, 33b, 34a, 34b, 35a, 35b, 46a, 46b, 51a, 51 b, 58a, 58b, 69a, 69b, 70a and 70b from above are tested in vivo to measure its ability to reduce intraocular pressure. Compound 14a is tested in normotensive dogs. The intraocular pressure (IOP) decreases from baseline. This compound is also tested in laser-induced hypertensive monkeys, the IOP decreases from baseline.

Compound 14b is tested in normotensive dogs. The intraocular pressure (IOP) decreases from baseline. This compound is also tested in laser-induced hypertensive monkeys, the IOP decreases from baseline.

Compound 16a is tested in normotensive dogs. The intraocular pressure (IOP) decreases from baseline. This compound is also tested in laser-induced hypertensive monkeys, the IOP decreases from baseline.

Compound 16b is tested in normotensive dogs. The intraocular pressure (IOP) decreases from baseline. This compound is also tested in laser-induced hypertensive monkeys, the IOP decreases from baseline.

Compound 22a is tested in normotensive dogs. The intraocular pressure (IOP) decreases from baseline. This compound is also tested in laser-induced hypertensive monkeys, the IOP decreases from baseline.

Compound 22b is tested in normotensive dogs. The intraocular pressure (IOP) decreases from baseline. This compound is also tested in laser-induced hypertensive monkeys, the IOP decreases from baseline.

Compound 33a is tested in normotensive dogs. The intraocular pressure (IOP) decreases from baseline. This compound is also tested in laser-induced hypertensive monkeys, the IOP decreases from baseline.

Compound 33b is tested in normotensive dogs. The intraocular pressure (IOP) decreases from baseline. This compound is also tested in laser-induced hypertensive monkeys, the IOP decreases from baseline.

Compound 34a is tested in normotensive dogs. The intraocular pressure (IOP) decreases from baseline. This compound is also tested in laser-induced hypertensive monkeys, the IOP decreases from baseline.

Compound 34b is tested in normotensive dogs. The intraocular pressure (IOP) decreases from baseline. This compound is also tested in laser-induced hypertensive monkeys, the IOP decreases from baseline.

Compound 35a is tested in normotensive dogs. The intraocular pressure (IOP) decreases from baseline. This compound is also tested in laser-induced hypertensive monkeys, the IOP decreases from baseline.

Compound 35b is tested in normotensive dogs. The intraocular pressure (IOP) decreases from baseline. This compound is also tested in laser-induced hypertensive monkeys, the IOP decreases from baseline.

Compound 46a is tested in normotensive dogs. The intraocular pressure (IOP) decreases from baseline. This compound is also tested in laser-induced hypertensive monkeys, the IOP decreases from baseline.

Compound 46b is tested in normotensive dogs. The intraocular pressure (IOP) decreases from baseline. This compound is also tested in laser-induced hypertensive monkeys, the IOP decreases from baseline.

Compound 51a is tested in normotensive dogs. The intraocular pressure (IOP) decreases from baseline. This compound is also tested in laser-induced hypertensive monkeys, the IOP decreases from baseline.

Compound 51 b is tested in normotensive dogs. The intraocular pressure (IOP) decreases from baseline. This compound is also tested in laser-induced hypertensive monkeys, the IOP decreases from baseline.

Compound 58a is tested in normotensive dogs. The intraocular pressure (IOP) decreases from baseline. This compound is also tested in laser-induced hypertensive monkeys, the IOP decreases from baseline.

Compound 58b is tested in normotensive dogs. The intraocular pressure (IOP) decreases from baseline. This compound is also tested in laser-induced hypertensive monkeys, the IOP decreases from baseline.

Compound 69a is tested in normotensive dogs. The intraocular pressure (IOP) decreases from baseline. This compound is also tested in laser-induced hypertensive monkeys, the IOP decreases from baseline.

Compound 69b is tested in normotensive dogs. The intraocular pressure (IOP) decreases from baseline. This compound is also tested in laser-induced hypertensive monkeys, the IOP decreases from baseline.

Compound 70a is tested in normotensive dogs. The intraocular pressure (IOP) decreases from baseline. This compound is also tested in laser-induced hypertensive monkeys, the IOP decreases from baseline.

Compound 70b is tested in normotensive dogs. The intraocular pressure (IOP) decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

[structure shown with substituents A—Y, O—B, and G on a cyclopentene ring]

or a pharmaceutically acceptable salt thereof or a prodrug thereof;

wherein Y is

[structure: -C(=O)-O-CH₂CH₂-OH] or

[structure: -C(=O)-O-CH₂CH₂-N-morpholine];

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH=CH— or —C≡C—;

G is H or OH; and

B is aryl or heteroaryl.

2. The compound of claim 1 wherein A has a structure selected from

[various heteroarylene linker structures shown including thiazole, oxazole, furan, thiophene with various alkyl, alkenyl, alkynyl, ether, thioether and phenyl linkages]

3. The compound of claim 2 wherein A is 5-(3-propyl)thiophen-2-yl.

4. The compound of claim 1 wherein A is 6-hexyl.

5. The compound of claim 1 wherein A is (Z)-6-hex-4-enyl.

6. The compound of claim 1 wherein B is a substituted phenyl.

7. The compound of claim 1 of the formula

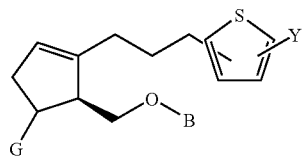

or a pharmaceutically acceptable salt thereof or a prodrug thereof.

8. The compound of claim 7 of the formula

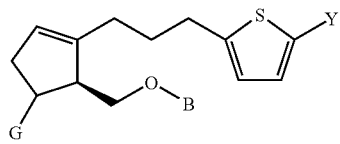

or a pharmaceutically acceptable salt thereof or a prodrug thereof.

9. The compound of claim 1 of the formula

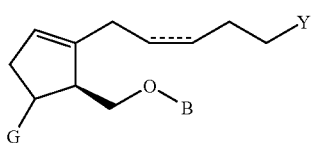

or a pharmaceutically acceptable salt thereof or a prodrug thereof;

wherein a dashed line represents the presence or absence of a bond.

10. The compound of claim 1 of the formula

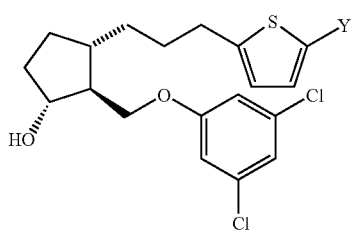

or a pharmaceutically acceptable salt thereof or a prodrug thereof.

11. A method for treating baldness comprising administering to a subject in need thereof a therapeutically effective amount of a compound according to claim 1.

* * * * *

UNITED STATES PATENT AND TRADEMARK OFFICE
CERTIFICATE OF CORRECTION

PATENT NO.           : 7,803,797 B2  
APPLICATION NO.      : 12/427803  
DATED                : September 28, 2010  
INVENTOR(S)          : David W. Old et al.

It is certified that error appears in the above-identified patent and that said Letters Patent is hereby corrected as shown below:

On the title page, item 56, under "Other Publications", in column 2, line 10, delete "Biorganic" and insert -- Bioorganic --, therefor.

In the specification

In column 1, line 9, after "reference" insert -- . --.

In column 1, line 34, delete "pupilary" and insert -- pupillary --, therefor.

In column 2, line 42, delete "Chrohn's" and insert -- Crohn's --, therefor.

In column 2, line 43, delete "varialoforme," and insert -- varioliform, --, therefor.

In column 2, line 47, delete "crythematosus," and insert -- erythematosus, --, therefor.

In column 2, line 49, delete "Sjgren's" and insert -- Sjogren's --, therefor.

In column 2, line 51, delete "neohropathy," and insert -- nephropathy, --, therefor.

In column 2, line 54, delete "Alzheimers" and insert -- Alzheimer's --, therefor.

In column 2, line 62, delete "periodonritis," and insert -- periodontitis, --, therefor.

In column 3, line 3, delete "EP2" and insert -- $EP_2$ --, therefor.

In column 7, line 17, delete "1$CH_2$" and insert -- 1 $CH_2$ --, therefor.

In column 9, line 43, delete "—$CH_2CH{\equiv}CH$—" and insert -- —$CH_2CH{=}CH$— --, therefor.

Signed and Sealed this  
First Day of March, 2016

Michelle K. Lee  
*Director of the United States Patent and Trademark Office*

In the specification

In column 9, line 49, delete "—(CH2)$_4$—." and insert -- —(CH$_2$)$_4$—. --, therefor.

In column 11, line 30, after " 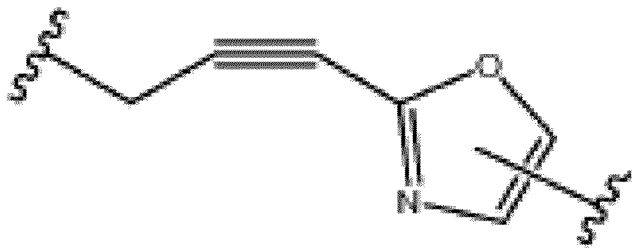 " insert -- . --.

In column 12, line 50, delete "no" and insert -- not --, therefor.

In column 13, line 2, delete "akynyl" and insert -- alkynyl --, therefor.

In column 26, line 18, delete "such" and insert -- Such --, therefor.

In column 26, line 29, delete "matricies" and insert -- matrices --, therefor.

In column 26, line 43, delete "betain," and insert -- betaine, --, therefor.

In column 26, line 44, delete "matricies" and insert -- matrices --, therefor.

In column 26, line 53, delete "anti oxidants." and insert -- antioxidants. --, therefor.

In column 30, line 29, below "DIAD, PPh$_3$" delete "9.CH$_2$Cl$_2$" and insert -- 9,CH$_2$Cl$_2$ --.

In column 31, line 52, delete "12(13" and insert -- 12 (13 --, therefor.

In column 34, line 60, delete "in" and insert -- 21 in --, therefor.

In column 37, line 10, after "2" insert -- . --.

In column 41, line 53, delete "ClCO$_2$" and insert -- ClCO$_2$Et, --, therefor.

In column 43, line 50, delete "ClCO$_2$" and insert -- ClCO$_2$Et, --, therefor.

In column 47, line 56, delete "Disilylation" and insert -- Desilylation --, therefor.

In column 49, line 23, delete "16b." and insert -- 16b, --, therefor.

In column 49, line 24, delete "51 b," and insert -- 51b, --, therefor.

In column 50, line 22, delete "51 b," and insert -- 51b, --, therefor.

CERTIFICATE OF CORRECTION (continued)
U.S. Pat. No. 7,803,797 B2

In the claims

In column 51, line 35, in claim 1, delete "—C=C—;" and insert -- —C≡C—; --, therefor.

In column 54, line 15, in claim 1, delete " 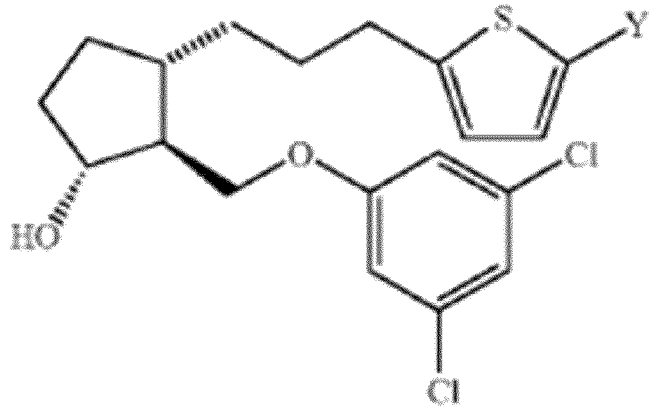 "

and insert -- 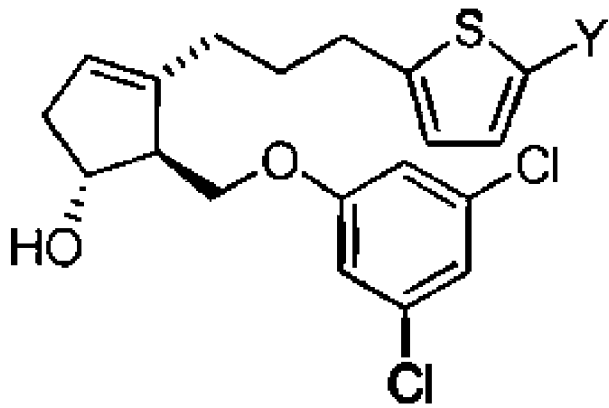 --, therefor.